US010886007B2

(12) United States Patent
Colavin et al.

(10) Patent No.: US 10,886,007 B2
(45) Date of Patent: Jan. 5, 2021

(54) METHODS AND SYSTEMS FOR IDENTIFICATION OF BIOMOLECULE SEQUENCE COEVOLUTION AND APPLICATIONS THEREOF

(71) Applicant: The Board of Trustees of the Leland Stanford Junior University, Stanford, CA (US)

(72) Inventors: Alexandre Colavin, Stanford, CA (US); Kerwyn Casey Huang, Menlo Park, CA (US); Carlos L. Araya, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 618 days.

(21) Appl. No.: 15/360,947

(22) Filed: Nov. 23, 2016

(65) Prior Publication Data
US 2017/0220734 A1    Aug. 3, 2017

Related U.S. Application Data

(60) Provisional application No. 62/258,969, filed on Nov. 23, 2015.

(51) Int. Cl.
*G16B 40/00*    (2019.01)
*G16B 10/00*    (2019.01)

(52) U.S. Cl.
CPC ............ *G16B 40/00* (2019.02); *G16B 10/00* (2019.02)

(58) Field of Classification Search
None
See application file for complete search history.

(56) References Cited

U.S. PATENT DOCUMENTS

2013/0303387 A1    11/2013    Sander et al.

OTHER PUBLICATIONS

Tamura et al. MEGA5: Molecular Evolutionary Genetics Analysis Using Maximum Likelihood, Evolutionary Distance, and Maximum Parsimony Methods Molecular Biology and Evolution vol. 28, pp. 2731-2739 (Year: 2011).*
Fares et al. A Novel Method for Detecting Intramolecular Coevolution: Adding a Further Dimension to Selective Constraints Analyses Genetics vol. 173 pp. 9-23 (Year: 2006).*
Hamosh et al. Online Mendelian Inheritance in Man (OMIM), a knowledgebase of human genes and genetic disorders Nucleic Acids Research vol. 33 pp. D514-D517 (Year: 2005).*
Bao et al. Prediction of the phenotypic effects of non-synonymous single nucleotide polymorphisms using structural and evolutionary information Bioinformatics vol. 21 pp. 2185-2190 (Year: 2005).*
Jimenez-Sanchez et al. Human Disease Genes Nature vol. 409, pp. 853-855 (Year: 2001).*
Burton Inborn Errors of Metabolism in Infancy: A Guide to Diagnosis Pediatrics vol. 102 pp. 1-9 (Year: 1998).*
Naldini Gene therapy returns to centre stage Nature vol. 526 pp. 351-360 (Year: 2015).*
Comaniciu et al., "Mean shift: A robust approach toward feature space analysis", IEEE Pattern Analysis and Machine Intelligence, vol. 24, Issue 5; May 2002; p. 603-609.
De Juan et al., "Emerging methods in protein co-evolution", Nature Reviews, Genetics, 2013, No. 14, pp. 249-261 (author version).
Dunn et al., "Mutual information without the influence of phylogeny or entropy dramatically improves residue contact prediction", Bioinformatics, 2008, vol. 24, No. 3, pp. 333-340.
Dutheil et al., "Detecting groups of coevolving positions in a molecule: a clustering approach", BMC Evolutionary Biology, Nov. 30, 2007, vol. 7, 18 pgs.
Dwyer et al., "Predicting Functionally Informative Mutations in *Escherichia coli* BamA Using Evolutionary Covariance Analysis", Genetics, Oct. 2013, vol. 195, pp. 443-455.
Dye et al., "Mutations in the nucleotide binding pocket of MreB can alter cell curvature and polar morphology in Caulobacter", Molecular Microbiology, May 25, 2011, No. 81, No. 2, pp. 368-394.
Fodor et al., "Influence of Conservation on Calculations of Amino Acid Covariance in Multiple Sequence Alignments", Proteins: Structure, Function, and Bioinformatics, May 14, 2004, vol. 56, pp. 211-221.
Gitai et al., "An actin-like gene can determine cell polarity in bacteria", PNAS, Jun. 8, 2004, vol. 101, No. 23, pp. 8643-8648.
Gitai et al., "MreB Actin-Mediated Segregation of a Specific Region of a Bacterial Chromosome", Cell, Feb. 11, 2005, vol. 120, 319-341.
Gobel et al., "Correlated Mutations and Residue Contact in Proteins", Proteins: Structure, Function, and Genetics, 1994, vol. 18, pp. 309-317.
Guevara-Coto et al., "Protein sector analysis for the clustering of disease-associated mutations", BMC Genomics, Jul. 21-24, 2014, vol. 15 (Suppl 11):54, 7 pgs.
Halabi et al., "Protein Sectors: Evolutionary Units of Three-Dimensional Structure", Cell, Aug. 21, 2009, vol. 138, pp. 774-786.
Hollstein et al., "p53 Mutations in Human Cancers", Science, Jul. 5, 1991, vol. 253, pp. 49-53.
Hopf et al., "Quantification of the effect of mutations using a global probability model of natural sequence variation", arXiv, 2015, http://arxiv.org/abs/1510.04612, 26 pgs.
Jordan et al., "Identification of cis-suppression of human disease mutations by comparative genomics", Nature, Aug. 13, 2015, vol. 524, pp. 11 pgs.

(Continued)

*Primary Examiner* — John S Brusca
(74) *Attorney, Agent, or Firm* — KPPB LLP

(57) ABSTRACT

Generation of biomolecule sequence coevolution data structures, matrices, scores, and sectors are described. Generally, the generated coevolution data removes covariant noise due to phylogenetic drift and can reveal coevolution of residue positions in multiple phylogenetic distances. Scores can be built upon the data structures and matrices to reveal sectors of residue positions that function and evolve together. Furthermore, the coevolution data structures, matrices, scores, and sectors can be used to predict structure or function of residue variants.

12 Claims, 22 Drawing Sheets
(17 of 22 Drawing Sheet(s) Filed in Color)

Specification includes a Sequence Listing.

(56) References Cited

OTHER PUBLICATIONS

Kotaka et al., "Structural studies of glucose-6-phosphate and NADP binding to human glucose-6-phosphate dehydrogenase", Acta Cryst., Jan. 21, 2005, vol. D61, pp. 495-504 Section D.

Kotsiantis, "Supervised Machine Learning: A Review of Classification Techniques", Informatica, Jul. 16, 2007, vol. 31, pp. 249-268.

Kruse et al., "Dysfunctional MreB inhibits chromosome segregation in *Escherichia coli*", The EMBO Journal, Aug. 12, 2003, vol. 22, No. 19, pp. 5283-5292.

Lockless et al., "Evolutionary Conserved Pathways of Energetic Connectivity in Protein Families", Science, Oct. 8, 1999, vol. 286, pp. 295-299.

Monds et al., "Systematic Perturbation of cytoskeletal Function Reveals a Linear Scaling Relationship between Cell Geometry and Fitness", Cell Reports, Nov. 20, 2014, vol. 9, pp. 1528-1537.

Morcos et al., "Coevolutionary signals across protein lineages help capture multiple protein conformations", PNAS, Dec. 17, 2013, vol. 110, No. 51, pp. 20533-20538.

Morcos et al., "Direct-coupling analysis of residue coevolution captures native contacts across many protein families", PNAS, Dec. 6, 2011, vol. 108, No. 49, pp. E1293-E1301.

Neher, "How frequent are correlated changes in families of protein sequences?", Biochemistry, Proc. Natl. Acad. Sci. USA, Jan. 1994, vol. 91, pp. 98-102.

Ovchinnikov et al., "Robust and accurate prediction of residue-residue interactions across protein interfaces using evolutionary information", eLife, May 1, 2014, pp. 1-21.

Reynolds et al., "Hot Spots for Allosteric Regulation on Protein Surfaces", Cell, Dec. 23, 2011, vol. 147, pp. 1564-1575.

Shiomi et al., "Mutations in cell elongation genes mreB, mrdA and mrdB suppress the shape defect of RodZ-deficient cells", Molecular Microbiology, Jan. 21, 2013, vol. 87m No. 5, pp. 1029-1044.

Skerker et al., "Rewiring the Specificity of Two-Component Signal Transduction Systems", Cell, Jun. 13, 2008, vol. 133, pp. 1043-1054.

Sulkowska et al., "Genomics-aided structure prediction", PNAS, Jun. 26, 2012, vol. 109, No. 26, 6 pgs.

Talavera et al., "Covariation Is a Poor Measure of Molecular Coevolution", Mol. Biol. Evol., May 4, 2015, vol. 32, No. 9, pp. 2456-2468.

Tesileanu et al., "Protein sectors: statistical coupling analysis versus conservation", PLoS Computational Biology, Feb. 27, 2015, vol. 11, No. 2, 33 pgs.

Van Den Ent et al., "Bacterial actin MreB forms antiparallel double filaments", eLIFE, May 2, 2014, 22 pgs.

Zvelebil et al., "Prediction of protein secondary structure and active sites using the alignment of homologous sequences", Journal of Molecular Biology, 1987, vol. 195, pp. 957-961.

* cited by examiner

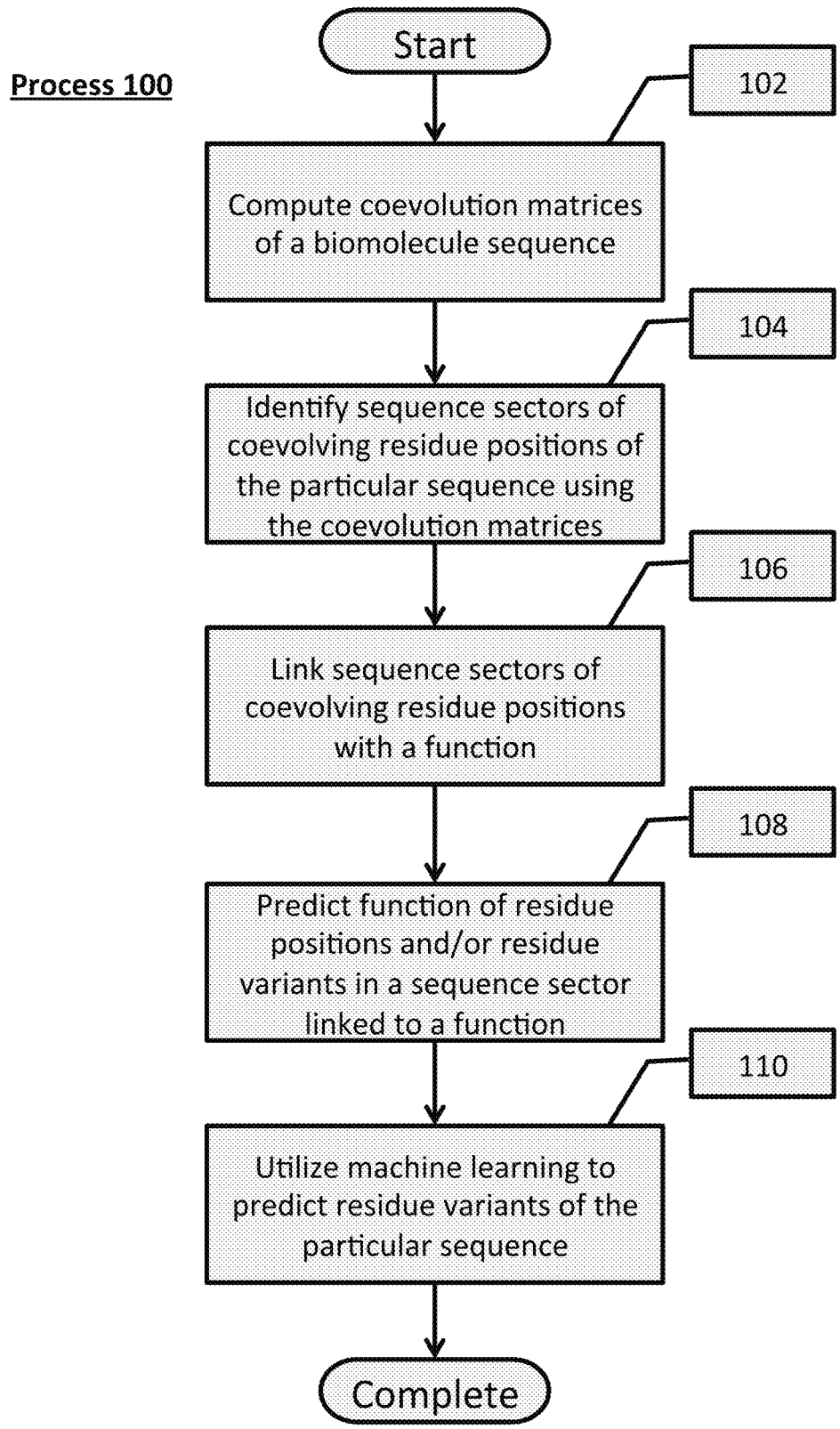

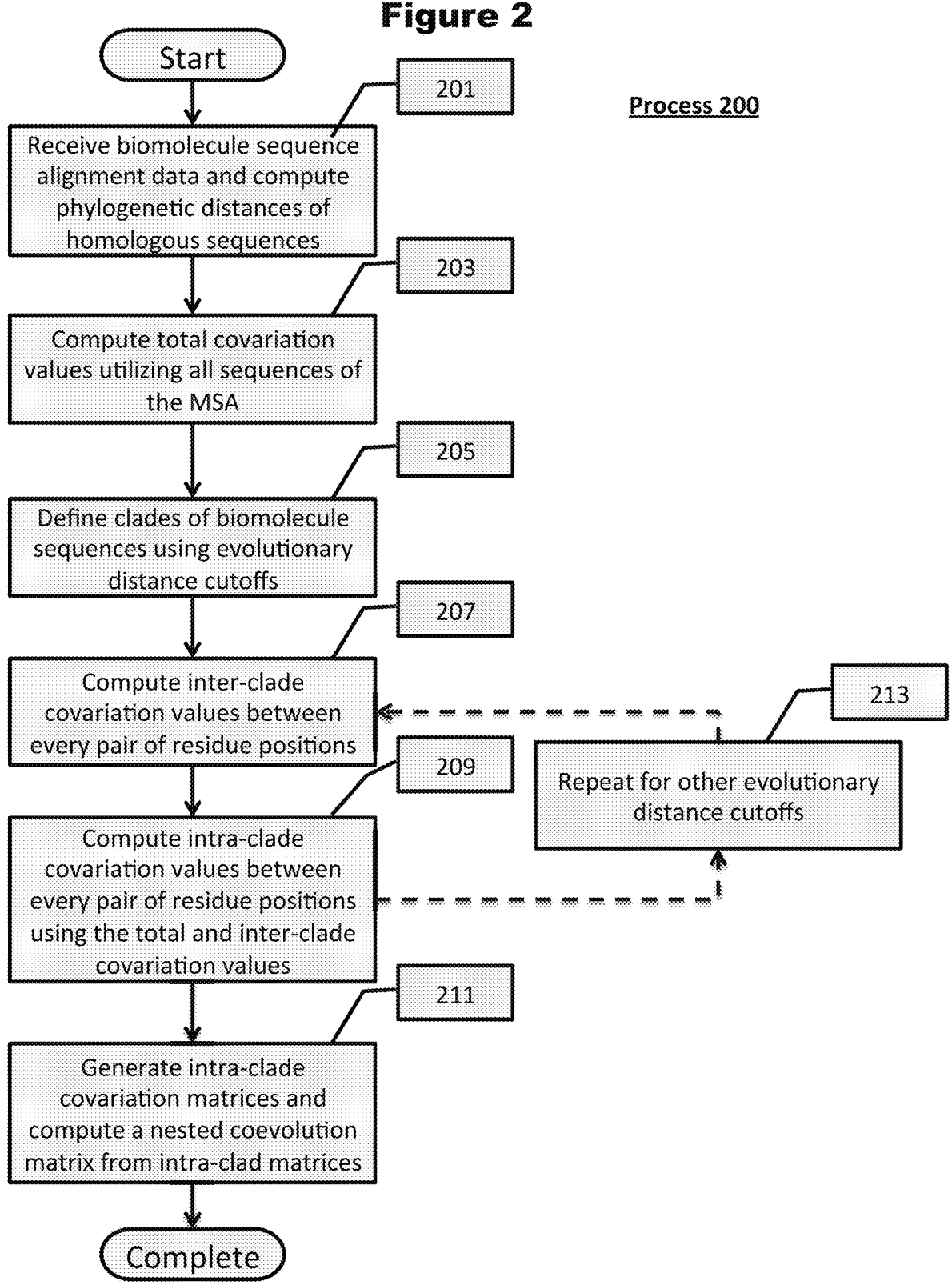

Figure 3

```
MGLGKTVQALALISCYREEWPCLILVPTSLRDAWHEALFRWLDVRLSGLIASVGSGAEADG
MGLGKTIQAIAVASYYRSDWPLLVVCPSSLKISWAEAF?RWIPS?LSKDINVIMTMKCP??
MGLGKTIQAICVAAFYRKEWPLLVVVPSSVRFTWEQAF?QWLPSLSPDHINVVVTGK??DH
MGLGKTLQALALMAFYKDDWPFIVVCPSSIRFQWKDQA?RWLSHLIREHICVVKNGKT?DI
MGLGKTIQAICIAAFYRNEWPLLVVVPSSVRFTWEQAF?QWLPSLRPDNINVVVKGK??DS
MGLGKTVQALAIAAAYRSEWPLLVVAPLSLRWAWREAA?RWLGLPPLADIH???????HQ
MGLGKTVQAICIAAYYRDEWPLLVVSPSSVRFTWAEAF?RWLPSLSPDSINVVVKAK??DN
MGLGKTIQAICIAAYYKKEWPLLVVTPSSVRFTWAEAF?RWLPSLTPDSINVVVKAK??DG
MGLGKTLQALALMAFYKDDWPFIVVCPSSIRFQWKDQA?RWLSHLIREHICVVKNGKT?DI
MGLGKTVQACALLACYKDECPALILVPTSLREAWRNAL?SWLDA??DGDIAVVGAANEA??
MGLGKTLQALALMAFYNKDWPFIVICPSSIRFQWKDQA?RWLPHLIEKDICVIKSGKM?DI
MGLGKTVQAICIAAYYRNEWPLLVVTPSSVRFTWAEAF?RWLPSLSPDSINVAVKAK??EN
MGLGKTLQALALMAFYNKDWPFIVVCPSSIRFQWKDQA?RWLPHLIEKDICVIKSGKM?DI
MGLGKTLQALALMAFYQEDWPFIVVCPSSIRFQWKDQA?RWLSHLLSDEICVVKSGKT?NI
```

Figure 4

```
SEQUENCE LISTING

<160> NUMBER OF SEQ ID NOS: 17

<210> SEQ ID NO 1
<211> LENGTH: 61
<212> TYPE: PRT
<213> ORGANISM: Artificial Sequence
<220> FEATURE:
<223> OTHER INFORMATION: provided as exemplary sequence alignment

<400> SEQUENCE: 1

Met Gly Leu Gly Lys Thr Val Gln Ala Leu Ala Leu Ile Ser Cys Tyr
1               5                   10                  15

Arg Glu Glu Trp Pro Cys Leu Ile Leu Val Pro Thr Ser Leu Arg Asp
                20                  25                  30

Ala Trp His Glu Ala Leu Phe Arg Trp Leu Asp Val Arg Leu Ser Gly
            35                  40                  45

Leu Ile Ala Ser Val Gly Ser Gly Ala Glu Ala Asp Gly
        50                  55                  60

<210> SEQ ID NO 2
<211> LENGTH: 61
<212> TYPE: PRT
<213> ORGANISM: Artificial Sequence
<220> FEATURE:
<223> OTHER INFORMATION: provided as exemplary sequence alignment
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
```

```
<220> FEATURE:
<221> NAME/KEY: misc_feature
<222> LOCATION: (60)..(61)
<223> OTHER INFORMATION: Xaa can be any naturally occurring amino acid

<400> SEQUENCE: 2

Met Gly Leu Gly Lys Thr Ile Gln Ala Ile Ala Val Ala Ser Tyr Tyr
1               5                   10                  15

Arg Ser Asp Trp Pro Leu Leu Val Val Cys Pro Ser Ser Leu Lys Ile
            20                  25                  30

Ser Trp Ala Glu Ala Phe Xaa Arg Trp Ile Pro Ser Xaa Leu Ser Lys
        35                  40                  45

Asp Ile Asn Val Ile Met Thr Met Lys Cys Pro Xaa Xaa
    50                  55                  60

<210> SEQ ID NO 3
<211> LENGTH: 61
<212> TYPE: PRT
<213> ORGANISM: Artificial Sequence
<220> FEATURE:
<223> OTHER INFORMATION: provided as exemplary sequence alignment
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (58)..(59)
<223> OTHER INFORMATION: Xaa can be any naturally occurring amino acid

<400> SEQUENCE: 3

Met Gly Leu Gly Lys Thr Ile Gln Ala Ile Cys Val Ala Ala Phe Tyr
1               5                   10                  15

Arg Lys Glu Trp Pro Leu Leu Val Val Val Pro Ser Ser Val Arg Phe
            20                  25                  30

Thr Trp Glu Gln Ala Phe Xaa Gln Trp Leu Pro Ser Leu Ser Pro Asp
        35                  40                  45

His Ile Asn Val Val Val Thr Gly Lys Xaa Xaa Asp His
    50                  55                  60

<210> SEQ ID NO 4
<211> LENGTH: 61
<212> TYPE: PRT
<213> ORGANISM: Artificial Sequence
<220> FEATURE:
<223> OTHER INFORMATION: provided as exemplary sequence alignment
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid

<400> SEQUENCE: 4

Met Gly Leu Gly Lys Thr Leu Gln Ala Leu Ala Leu Met Ala Phe Tyr
1               5                   10                  15

Lys Asp Asp Trp Pro Phe Ile Val Val Cys Pro Ser Ser Ile Arg Phe
            20                  25                  30

Gln Trp Lys Asp Gln Ala Xaa Arg Trp Leu Ser His Leu Leu Ile Arg
        35                  40                  45

Glu His Ile Cys Val Val Lys Gly Lys Thr Xaa Asp Ile
    50                  55                  60
```

<210> SEQ ID NO 5
<211> LENGTH: 61
<212> TYPE: PRT
<213> ORGANISM: Artificial Sequence
<220> FEATURE:
<223> OTHER INFORMATION: provided as exemplary sequence alignment
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (58)..(59)
<223> OTHER INFORMATION: Xaa can be any naturally occurring amino acid

<400> SEQUENCE: 5

Met Gly Leu Gly Lys Thr Ile Gln Ala Ile Cys Ile Ala Ala Phe Tyr
1               5                   10                  15

Arg Asn Glu Trp Pro Leu Leu Val Val Pro Ser Ser Val Arg Phe
                20                  25                  30

Thr Trp Glu Gln Ala Phe Xaa Gln Trp Leu Pro Ser Leu Arg Pro Asp
            35                  40                  45

Asn Ile Asn Val Val Val Lys Gly Lys Xaa Xaa Asp Ser
    50                  55                  60

<210> SEQ ID NO 6
<211> LENGTH: 61
<212> TYPE: PRT
<213> ORGANISM: Artificial Sequence
<220> FEATURE:
<223> OTHER INFORMATION: provided as exemplary sequence alignment
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (52)..(59)
<223> OTHER INFORMATION: Xaa can be any naturally occurring amino acid

<400> SEQUENCE: 6

Met Gly Leu Gly Lys Thr Val Gln Ala Leu Ala Ile Ala Ala Tyr
1               5                   10                  15

Arg Ser Glu Trp Pro Leu Leu Val Val Ala Pro Leu Ser Leu Arg Trp
                20                  25                  30

Ala Trp Arg Glu Ala Ala Xaa Arg Trp Leu Gly Leu Pro Pro Leu Ala
            35                  40                  45

Asp Ile His Xaa Xaa Xaa Xaa Xaa Xaa Xaa Xaa His Gln
    50                  55                  60

<210> SEQ ID NO 7
<211> LENGTH: 61
<212> TYPE: PRT
<213> ORGANISM: Artificial Sequence
<220> FEATURE:
<223> OTHER INFORMATION: provided as exemplary sequence alignment
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (58)..(59)
<223> OTHER INFORMATION: Xaa can be any naturally occurring amino acid

<400> SEQUENCE: 7

Met Gly Leu Gly Lys Thr Val Gln Ala Ile Cys Ile Ala Ala Tyr Tyr

```
                1               5                   10                  15
Arg Asp Glu Trp Pro Leu Leu Val Val Ser Pro Ser Ser Val Arg Phe
            20                  25                  30

Thr Trp Ala Glu Ala Phe Xaa Arg Trp Leu Pro Ser Leu Ser Pro Asp
        35                  40                  45

Ser Ile Asn Val Val Val Lys Ala Lys Xaa Xaa Asp Asn
    50                  55                  60
```

<210> SEQ ID NO 8
<211> LENGTH: 61
<212> TYPE: PRT
<213> ORGANISM: Artificial Sequence
<220> FEATURE:
<223> OTHER INFORMATION: provided as exemplary sequence alignment
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (58)..(59)
<223> OTHER INFORMATION: Xaa can be any naturally occurring amino acid

<400> SEQUENCE: 8

```
Met Gly Leu Gly Lys Thr Ile Gln Ala Ile Cys Ile Ala Ala Tyr Tyr
1               5                   10                  15

Lys Lys Glu Trp Pro Leu Leu Val Val Thr Pro Ser Ser Val Arg Phe
            20                  25                  30

Thr Trp Ala Glu Ala Phe Xaa Arg Trp Leu Pro Ser Leu Thr Pro Asp
        35                  40                  45

Ser Ile Asn Val Val Val Lys Ala Lys Xaa Xaa Asp Gly
    50                  55                  60
```

<210> SEQ ID NO 9
<211> LENGTH: 61
<212> TYPE: PRT
<213> ORGANISM: Artificial Sequence
<220> FEATURE:
<223> OTHER INFORMATION: provided as exemplary sequence alignment
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid

<400> SEQUENCE: 9

```
Met Gly Leu Gly Lys Thr Leu Gln Ala Leu Ala Leu Met Ala Phe Tyr
1               5                   10                  15

Lys Asp Asp Trp Pro Phe Ile Val Val Cys Pro Ser Ser Ile Arg Phe
            20                  25                  30

Gln Trp Lys Asp Gln Ala Xaa Arg Trp Leu Ser His Leu Ile Arg Glu
        35                  40                  45

His Ile Cys Val Val Lys Asn Gly Lys Thr Xaa Asp Ile
    50                  55                  60
```

<210> SEQ ID NO 10
<211> LENGTH: 61
<212> TYPE: PRT
<213> ORGANISM: Artificial Sequence
<220> FEATURE:
<223> OTHER INFORMATION: provided as exemplary sequence alignment
<220> FEATURE:

```
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (45)..(46)
<223> OTHER INFORMATION: Xaa can be any naturally occurring amino acid
<220> FEATURE:
<221> NAME/KEY: misc_feature
<222> LOCATION: (60)..(61)
<223> OTHER INFORMATION: Xaa can be any naturally occurring amino acid

<400> SEQUENCE: 10

Met Gly Leu Gly Lys Thr Val Gln Ala Cys Ala Leu Ala Cys Tyr
1               5                   10                  15

Lys Asp Glu Cys Pro Ala Leu Ile Leu Val Pro Thr Ser Leu Arg Glu
                20                  25                  30

Ala Trp Arg Asn Ala Leu Xaa Ser Trp Leu Asp Ala Xaa Xaa Asp Gly
            35                  40                  45

Asp Ile Ala Val Val Gly Ala Ala Asn Glu Ala Xaa Xaa
        50                  55                  60

<210> SEQ ID NO 11
<211> LENGTH: 61
<212> TYPE: PRT
<213> ORGANISM: Artificial Sequence
<220> FEATURE:
<223> OTHER INFORMATION: provided as exemplary sequence alignment
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid

<400> SEQUENCE: 11

Met Gly Leu Gly Lys Thr Leu Gln Ala Leu Ala Leu Met Ala Phe Tyr
1               5                   10                  15

Asn Lys Asp Trp Pro Phe Ile Val Ile Cys Pro Ser Ser Ile Arg Phe
                20                  25                  30

Gln Trp Lys Asp Gln Ala Xaa Arg Trp Leu Pro His Leu Ile Glu Lys
            35                  40                  45

Asp Ile Cys Val Ile Lys Ser Gly Lys Met Xaa Asp Ile
        50                  55                  60

<210> SEQ ID NO 12
<211> LENGTH: 61
<212> TYPE: PRT
<213> ORGANISM: Artificial Sequence
<220> FEATURE:
<223> OTHER INFORMATION: provided as exemplary sequence alignment
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (58)..(59)
<223> OTHER INFORMATION: Xaa can be any naturally occurring amino acid

<400> SEQUENCE: 12

Met Gly Leu Gly Lys Thr Val Gln Ala Ile Cys Ile Ala Ala Tyr Tyr
1               5                   10                  15

Arg Asn Glu Trp Pro Leu Leu Val Val Thr Pro Ser Ser Val Arg Phe
                20                  25                  30
```

```
Thr Trp Ala Glu Ala Phe Xaa Arg Trp Leu Pro Ser Leu Ser Pro Asp
        35                  40                  45

Ser Ile Asn Val Ala Val Lys Ala Lys Xaa Xaa Glu Asn
    50                  55                  60

<210> SEQ ID NO 13
<211> LENGTH: 61
<212> TYPE: PRT
<213> ORGANISM: Artificial Sequence
<220> FEATURE:
<223> OTHER INFORMATION: provided as exemplary sequence alignment
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid

<400> SEQUENCE: 13

Met Gly Leu Gly Lys Thr Leu Gln Ala Leu Ala Leu Met Ala Phe Tyr
1               5                   10                  15

Asn Lys Asp Trp Pro Phe Ile Val Val Cys Pro Ser Ser Ile Arg Phe
            20                  25                  30

Gln Trp Lys Asp Gln Ala Xaa Arg Trp Leu Pro His Leu Ile Glu Lys
        35                  40                  45

Asp Ile Cys Val Ile Lys Ser Gly Lys Met Xaa Asp Ile
    50                  55                  60

<210> SEQ ID NO 14
<211> LENGTH: 61
<212> TYPE: PRT
<213> ORGANISM: Artificial Sequence
<220> FEATURE:
<223> OTHER INFORMATION: provided as exemplary sequence alignment
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid

<400> SEQUENCE: 14

Met Gly Leu Gly Lys Thr Leu Gln Ala Leu Ala Leu Met Ala Phe Tyr
1               5                   10                  15

Gln Glu Asp Trp Pro Phe Ile Val Val Cys Pro Ser Ser Ile Arg Phe
            20                  25                  30

Gln Trp Lys Asp Gln Ala Xaa Arg Trp Leu Ser His Leu Leu Ser Asp
        35                  40                  45

Glu Ile Cys Val Val Lys Ser Gly Lys Thr Xaa Asn Ile
    50                  55                  60

<210> SEQ ID NO 15
<211> LENGTH: 374
<212> TYPE: PRT
<213> ORGANISM: Homo sapiens

<400> SEQUENCE: 15

Met Asp Asp Asp Ile Ala Ala Leu Val Val Asp Asn Gly Ser Gly Met
1               5                   10                  15

Cys Lys Ala Gly Phe Ala Gly Asp Asp Ala Pro Arg Ala Val Phe Pro
```

```
            20                  25                  30
Ser Ile Val Gly Arg Pro Arg His Gln Gly Val Met Val Gly Met Gly
         35                  40                  45
Gln Lys Asp Ser Tyr Val Gly Asp Glu Ala Gln Ser Lys Arg Gly Ile
 50                  55                  60
Leu Thr Leu Lys Tyr Pro Ile Glu His Gly Ile Val Thr Asn Trp Asp
 65                  70                  75                  80
Asp Met Glu Lys Ile Trp His His Thr Phe Tyr Asn Glu Leu Arg Val
                 85                  90                  95
Ala Pro Glu Glu His Pro Val Leu Leu Thr Glu Ala Pro Leu Asn Pro
            100                 105                 110
Lys Ala Asn Arg Glu Lys Met Thr Gln Ile Met Phe Glu Thr Phe Asn
            115                 120                 125
Thr Pro Ala Met Tyr Val Ala Ile Gln Ala Val Leu Ser Leu Tyr Ala
            130                 135                 140
Ser Gly Arg Thr Thr Gly Ile Val Met Asp Ser Gly Asp Gly Val Thr
145                 150                 155                 160
His Thr Val Pro Ile Tyr Glu Gly Tyr Ala Leu Pro His Ala Ile Leu
                165                 170                 175
Arg Leu Asp Leu Ala Gly Arg Asp Leu Thr Asp Tyr Leu Met Lys Ile
            180                 185                 190
Leu Thr Glu Arg Gly Tyr Ser Phe Thr Thr Thr Ala Glu Arg Glu Ile
            195                 200                 205
Val Arg Asp Ile Lys Glu Lys Leu Cys Tyr Val Ala Leu Asp Phe Glu
            210                 215                 220
Gln Glu Met Ala Thr Ala Ala Ser Ser Ser Ser Leu Glu Lys Ser Tyr
225                 230                 235                 240
Glu Leu Pro Asp Gly Gln Val Ile Thr Ile Gly Asn Glu Arg Phe Arg
                245                 250                 255
Cys Pro Glu Ala Leu Phe Gln Pro Ser Phe Leu Gly Met Glu Ser Cys
            260                 265                 270
Gly Ile His Glu Thr Thr Phe Asn Ser Ile Met Lys Cys Asp Val Asp
            275                 280                 285
Ile Arg Lys Asp Leu Tyr Ala Asn Thr Val Leu Ser Gly Gly Thr Thr
            290                 295                 300
Met Tyr Pro Gly Ile Ala Asp Arg Met Gln Lys Glu Ile Thr Ala Leu
305                 310                 315                 320
Ala Pro Ser Thr Met Lys Ile Lys Ile Ile Ala Pro Pro Glu Arg Lys
                325                 330                 335
Tyr Ser Val Trp Ile Gly Gly Ser Ile Leu Ala Ser Leu Ser Thr Phe
            340                 345                 350
Gln Gln Met Trp Ile Ser Lys Gln Glu Tyr Asp Glu Ser Gly Pro Ser
            355                 360                 365
Ile Val His Arg Lys Cys
            370

<210> SEQ ID NO 16
<211> LENGTH: 1068
<212> TYPE: PRT
<213> ORGANISM: Homo sapiens

<400> SEQUENCE: 16

Met Pro Pro Arg Pro Ser Ser Gly Glu Leu Trp Gly Ile His Leu Met
 1               5                  10                  15
```

-continued

```
Pro Pro Arg Ile Leu Val Glu Cys Leu Leu Pro Asn Gly Met Ile Val
            20                  25                  30
Thr Leu Glu Cys Leu Arg Glu Ala Thr Leu Ile Thr Ile Lys His Glu
        35                  40                  45
Leu Phe Lys Glu Ala Arg Lys Tyr Pro Leu His Gln Leu Leu Gln Asp
    50                  55                  60
Glu Ser Ser Tyr Ile Phe Val Ser Val Thr Gln Glu Ala Glu Arg Glu
65                  70                  75                  80
Glu Phe Phe Asp Glu Thr Arg Arg Leu Cys Asp Leu Arg Leu Phe Gln
                85                  90                  95
Pro Phe Leu Lys Val Ile Glu Pro Val Gly Asn Arg Glu Glu Lys Ile
            100                 105                 110
Leu Asn Arg Glu Ile Gly Phe Ala Ile Gly Met Pro Val Cys Glu Phe
        115                 120                 125
Asp Met Val Lys Asp Pro Glu Val Gln Asp Phe Arg Arg Asn Ile Leu
    130                 135                 140
Asn Val Cys Lys Glu Ala Val Asp Leu Arg Asp Leu Asn Ser Pro His
145                 150                 155                 160
Ser Arg Ala Met Tyr Val Tyr Pro Pro Asn Val Glu Ser Ser Pro Glu
                165                 170                 175
Leu Pro Lys His Ile Tyr Asn Lys Leu Asp Lys Gly Gln Ile Ile Val
            180                 185                 190
Val Ile Trp Val Ile Val Ser Pro Asn Asn Asp Lys Gln Lys Tyr Thr
        195                 200                 205
Leu Lys Ile Asn His Asp Cys Val Pro Glu Gln Val Ile Ala Glu Ala
    210                 215                 220
Ile Arg Lys Lys Thr Arg Ser Met Leu Leu Ser Ser Glu Gln Leu Lys
225                 230                 235                 240
Leu Cys Val Leu Glu Tyr Gln Gly Lys Tyr Ile Leu Lys Val Cys Gly
                245                 250                 255
Cys Asp Glu Tyr Phe Leu Glu Lys Tyr Pro Leu Ser Gln Tyr Lys Tyr
            260                 265                 270
Ile Arg Ser Cys Ile Met Leu Gly Arg Met Pro Asn Leu Met Leu Met
        275                 280                 285
Ala Lys Glu Ser Leu Tyr Ser Gln Leu Pro Met Asp Cys Phe Thr Met
    290                 295                 300
Pro Ser Tyr Ser Arg Arg Ile Ser Thr Ala Thr Pro Tyr Met Asn Gly
305                 310                 315                 320
Glu Thr Ser Thr Lys Ser Leu Trp Val Ile Asn Ser Ala Leu Arg Ile
                325                 330                 335
Lys Ile Leu Cys Ala Thr Tyr Val Asn Val Asn Ile Arg Asp Ile Asp
            340                 345                 350
Lys Ile Tyr Val Arg Thr Gly Ile Tyr His Gly Gly Glu Pro Leu Cys
        355                 360                 365
Asp Asn Val Asn Thr Gln Arg Val Pro Cys Ser Asn Pro Arg Trp Asn
    370                 375                 380
Glu Trp Leu Asn Tyr Asp Ile Tyr Ile Pro Asp Leu Pro Arg Ala Ala
385                 390                 395                 400
Arg Leu Cys Leu Ser Ile Cys Ser Val Lys Gly Arg Lys Gly Ala Lys
                405                 410                 415
Glu Glu His Cys Pro Leu Ala Trp Gly Asn Ile Asn Leu Phe Asp Tyr
            420                 425                 430
Thr Asp Thr Leu Val Ser Gly Lys Met Ala Leu Asn Leu Trp Pro Val
```

```
            435                 440                 445
Pro His Gly Leu Glu Asp Leu Leu Asn Pro Ile Gly Val Thr Gly Ser
450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                485                 490                 495

Asn Trp Ser Val Ser Arg Glu Ala Gly Phe Ser Tyr Ser His Ala Gly
                500                 505                 510

Leu Ser Asn Arg Leu Ala Arg Asp Asn Glu Leu Arg Glu Asn Asp Lys
            515                 520                 525

Glu Gln Leu Lys Ala Ile Ser Thr Arg Asp Pro Leu Ser Glu Ile Thr
530                 535                 540

Glu Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
                565                 570                 575

Arg Asp Glu Val Ala Gln Met Tyr Cys Leu Val Lys Asp Trp Pro Pro
            580                 585                 590

Ile Lys Pro Glu Gln Ala Met Glu Leu Leu Asp Cys Asn Tyr Pro Asp
            595                 600                 605

Pro Met Val Arg Gly Phe Ala Val Arg Cys Leu Glu Lys Tyr Leu Thr
610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
            675                 680                 685

Glu Ser Tyr Cys Arg Ala Cys Gly Met Tyr Leu Lys His Leu Asn Arg
690                 695                 700

Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
                725                 730                 735

Glu Gln Met Arg Arg Pro Asp Phe Met Asp Ala Leu Gln Gly Phe Leu
            740                 745                 750

Ser Pro Leu Asn Pro Ala His Gln Leu Gly Asn Leu Arg Leu Glu Glu
            755                 760                 765

Cys Arg Ile Met Ser Ser Ala Lys Arg Pro Leu Trp Leu Asn Trp Glu
770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gly Leu Asp Leu Arg
            820                 825                 830

Met Leu Pro Tyr Gly Cys Leu Ser Ile Gly Asp Cys Val Gly Leu Ile
            835                 840                 845

Glu Val Val Arg Asn Ser His Thr Ile Met Gln Ile Gln Cys Lys Gly
850                 855                 860
```

-continued

```
Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
            885                 890                 895

Phe Thr Arg Ser Cys Ala Gly Tyr Cys Val Ala Thr Phe Ile Leu Gly
        900                 905                 910

Ile Gly Asp Arg His Asn Ser Asn Ile Met Val Lys Asp Asp Gly Gln
    915                 920                 925

Leu Phe His Ile Asp Phe Gly His Phe Leu Asp His Lys Lys Lys
930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Cys Thr Lys Thr Arg Glu
            965                 970                 975

Phe Glu Arg Phe Gln Glu Met Cys Tyr Lys Ala Tyr Leu Ala Ile Arg
        980                 985                 990

Gln His Ala Asn Leu Phe Ile Asn Leu Phe Ser Met Met Leu Gly Ser
    995                 1000                1005

Gly Met Pro Glu Leu Gln Ser Phe Asp Asp Ile Ala Tyr Ile Arg
    1010                1015                1020

Lys Thr Leu Ala Leu Asp Lys Thr Glu Gln Glu Ala Leu Glu Tyr
    1025                1030                1035

Phe Met Lys Gln Met Asn Asp Ala His His Gly Gly Trp Thr Thr
    1040                1045                1050

Lys Met Asp Trp Ile Phe His Thr Ile Lys Gln His Ala Leu Asn
    1055                1060                1065

<210> SEQ ID NO 17
<211> LENGTH: 1884
<212> TYPE: PRT
<213> ORGANISM: Homo sapiens

<400> SEQUENCE: 17

Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
            20                  25                  30

Glu Pro Val Ser Thr Lys Cys Asp His Ile Phe Cys Lys Phe Cys Met
        35                  40                  45

Leu Lys Leu Leu Asn Gln Lys Lys Gly Pro Ser Gln Cys Pro Leu Cys
    50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
            85                  90                  95

Thr Gly Leu Glu Tyr Ala Asn Ser Tyr Asn Phe Ala Lys Lys Glu Asn
        100                 105                 110

Asn Ser Pro Glu His Leu Lys Asp Glu Val Ser Ile Ile Gln Ser Met
    115                 120                 125

Gly Tyr Arg Asn Arg Ala Lys Arg Leu Leu Gln Ser Glu Pro Glu Asn
    130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
```

```
                165                 170                 175
Ser Val Tyr Ile Glu Leu Gly Ser Asp Ser Glu Asp Thr Val Asn
            180                 185                 190

Lys Ala Thr Tyr Cys Ser Val Gly Asp Gln Glu Leu Leu Gln Ile Thr
            195                 200                 205

Pro Gln Gly Thr Arg Asp Glu Ile Ser Leu Asp Ser Ala Lys Lys Ala
            210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
                245                 250                 255

His Pro Glu Lys Tyr Gln Gly Ser Ser Val Ser Asn Leu His Val Glu
                260                 265                 270

Pro Cys Gly Thr Asn Thr His Ala Ser Ser Leu Gln His Glu Asn Ser
                275                 280                 285

Ser Leu Leu Leu Thr Lys Asp Arg Met Asn Val Glu Lys Ala Glu Phe
            290                 295                 300

Cys Asn Lys Ser Lys Gln Pro Gly Leu Ala Arg Ser Gln His Asn Arg
305                 310                 315                 320

Trp Ala Gly Ser Lys Glu Thr Cys Asn Asp Arg Arg Thr Pro Ser Thr
                325                 330                 335

Glu Lys Lys Val Asp Leu Asn Ala Asp Pro Leu Cys Glu Arg Lys Glu
            340                 345                 350

Trp Asn Lys Gln Lys Leu Pro Cys Ser Glu Asn Pro Arg Asp Thr Glu
            355                 360                 365

Asp Val Pro Trp Ile Thr Leu Asn Ser Ser Ile Gln Lys Val Asn Glu
            370                 375                 380

Trp Phe Ser Arg Ser Asp Glu Leu Leu Gly Ser Asp Ser His Asp
385                 390                 395                 400

Gly Glu Ser Glu Ser Asn Ala Lys Val Ala Asp Val Leu Asp Val Leu
                405                 410                 415

Asn Glu Val Asp Glu Tyr Ser Gly Ser Ser Glu Lys Ile Asp Leu Leu
                420                 425                 430

Ala Ser Asp Pro His Glu Ala Leu Ile Cys Lys Ser Glu Arg Val His
            435                 440                 445

Ser Lys Ser Val Glu Ser Asn Ile Glu Asp Lys Ile Phe Gly Lys Thr
            450                 455                 460

Tyr Arg Lys Lys Ala Ser Leu Pro Asn Leu Ser His Val Thr Glu Asn
465                 470                 475                 480

Leu Ile Ile Gly Ala Phe Val Thr Glu Pro Gln Ile Ile Gln Glu Arg
                485                 490                 495

Pro Leu Thr Asn Lys Leu Lys Arg Lys Arg Arg Pro Thr Ser Gly Leu
            500                 505                 510

His Pro Glu Asp Phe Ile Lys Lys Ala Asp Leu Ala Val Gln Lys Thr
            515                 520                 525

Pro Glu Met Ile Asn Gln Gly Thr Asn Gln Thr Glu Gln Asn Gly Gln
            530                 535                 540

Val Met Asn Ile Thr Asn Ser Gly His Glu Asn Lys Thr Lys Gly Asp
545                 550                 555                 560

Ser Ile Gln Asn Glu Lys Asn Pro Asn Pro Ile Glu Ser Leu Glu Lys
                565                 570                 575

Glu Ser Ala Phe Lys Thr Lys Ala Glu Pro Ile Ser Ser Ser Ile Ser
            580                 585                 590
```

```
Asn Met Glu Leu Glu Leu Asn Ile His Asn Ser Lys Ala Pro Lys Lys
            595                 600                 605

Asn Arg Leu Arg Arg Lys Ser Ser Thr Arg His Ile His Ala Leu Glu
    610                 615                 620

Leu Val Val Ser Arg Asn Leu Ser Pro Pro Asn Cys Thr Glu Leu Gln
625                 630                 635                 640

Ile Asp Ser Cys Ser Ser Ser Glu Glu Ile Lys Lys Lys Lys Tyr Asn
                    645                 650                 655

Gln Met Pro Val Arg His Ser Arg Asn Leu Gln Leu Met Glu Gly Lys
            660                 665                 670

Glu Pro Ala Thr Gly Ala Lys Lys Ser Asn Lys Pro Asn Glu Gln Thr
            675                 680                 685

Ser Lys Arg His Asp Ser Asp Thr Phe Pro Glu Leu Lys Leu Thr Asn
    690                 695                 700

Ala Pro Gly Ser Phe Thr Lys Cys Ser Asn Thr Ser Glu Leu Lys Glu
705                 710                 715                 720

Phe Val Asn Pro Ser Leu Pro Arg Glu Glu Lys Glu Glu Lys Leu Glu
                    725                 730                 735

Thr Val Lys Val Ser Asn Asn Ala Glu Asp Pro Lys Asp Leu Met Leu
            740                 745                 750

Ser Gly Glu Arg Val Leu Gln Thr Glu Arg Ser Val Glu Ser Ser Ser
    755                 760                 765

Ile Ser Leu Val Pro Gly Thr Asp Tyr Gly Thr Gln Glu Ser Ile Ser
770                 775                 780

Leu Leu Glu Val Ser Thr Leu Gly Lys Ala Lys Thr Glu Pro Asn Lys
785                 790                 795                 800

Cys Val Ser Gln Cys Ala Ala Phe Glu Asn Pro Lys Gly Leu Ile His
                    805                 810                 815

Gly Cys Ser Lys Asp Asn Arg Asn Asp Thr Glu Gly Phe Lys Tyr Pro
            820                 825                 830

Leu Gly His Glu Val Asn His Ser Arg Glu Thr Ser Ile Glu Met Glu
            835                 840                 845

Glu Ser Glu Leu Asp Ala Gln Tyr Leu Gln Asn Thr Phe Lys Val Ser
    850                 855                 860

Lys Arg Gln Ser Phe Ala Pro Phe Ser Asn Pro Gly Asn Ala Glu Glu
865                 870                 875                 880

Glu Cys Ala Thr Phe Ser Ala His Ser Gly Ser Leu Lys Lys Gln Ser
                    885                 890                 895

Pro Lys Val Thr Phe Glu Cys Glu Gln Lys Glu Glu Asn Gln Gly Lys
            900                 905                 910

Asn Glu Ser Asn Ile Lys Pro Val Gln Thr Val Asn Ile Thr Ala Gly
            915                 920                 925

Phe Pro Val Val Gly Gln Lys Asp Lys Pro Val Asp Asn Ala Lys Cys
    930                 935                 940

Ser Ile Lys Gly Gly Ser Arg Phe Cys Leu Ser Ser Gln Phe Arg Gly
945                 950                 955                 960

Asn Glu Thr Gly Leu Ile Thr Pro Asn Lys His Gly Leu Leu Gln Asn
                    965                 970                 975

Pro Tyr Arg Ile Pro Pro Leu Phe Pro Ile Lys Ser Phe Val Lys Thr
            980                 985                 990

Lys Cys Lys Lys Asn Leu Leu Glu  Glu Asn Phe Glu Glu  His Ser Met
    995                 1000                1005
```

```
Ser Pro Glu Arg Glu Met Gly Asn Glu Asn Ile Pro Ser Thr Val
1010               1015                1020

Ser Thr Ile Ser Arg Asn Asn Ile Arg Glu Asn Val Phe Lys Glu
1025               1030                1035

Ala Ser Ser Ser Asn Ile Asn Glu Val Gly Ser Ser Thr Asn Glu
1040               1045                1050

Val Gly Ser Ser Ile Asn Glu Ile Gly Ser Ser Asp Glu Asn Ile
1055               1060                1065

Gln Ala Glu Leu Gly Arg Asn Arg Gly Pro Lys Leu Asn Ala Met
1070               1075                1080

Leu Arg Leu Gly Val Leu Gln Pro Glu Val Tyr Lys Gln Ser Leu
1085               1090                1095

Pro Gly Ser Asn Cys Lys His Pro Glu Ile Lys Lys Gln Glu Tyr
1100               1105                1110

Glu Glu Val Val Gln Thr Val Asn Thr Asp Phe Ser Pro Tyr Leu
1115               1120                1125

Ile Ser Asp Asn Leu Glu Gln Pro Met Gly Ser Ser His Ala Ser
1130               1135                1140

Gln Val Cys Ser Glu Thr Pro Asp Asp Leu Leu Asp Asp Gly Glu
1145               1150                1155

Ile Lys Glu Asp Thr Ser Phe Ala Glu Asn Asp Ile Lys Glu Ser
1160               1165                1170

Ser Ala Val Phe Ser Lys Ser Val Gln Lys Gly Glu Leu Ser Arg
1175               1180                1185

Ser Pro Ser Pro Phe Thr His Thr His Leu Ala Gln Gly Tyr Arg
1190               1195                1200

Arg Gly Ala Lys Lys Leu Glu Ser Ser Glu Glu Asn Leu Ser Ser
1205               1210                1215

Glu Asp Glu Glu Leu Pro Cys Phe Gln His Leu Leu Phe Gly Lys
1220               1225                1230

Val Asn Asn Ile Pro Ser Gln Ser Thr Arg His Ser Thr Val Ala
1235               1240                1245

Thr Glu Cys Leu Ser Lys Asn Thr Glu Glu Asn Leu Leu Ser Leu
1250               1255                1260

Lys Asn Ser Leu Asn Asp Cys Ser Asn Gln Val Ile Leu Ala Lys
1265               1270                1275

Ala Ser Gln Glu His His Leu Ser Glu Glu Thr Lys Cys Ser Ala
1280               1285                1290

Ser Leu Phe Ser Ser Gln Cys Ser Glu Leu Glu Asp Leu Thr Ala
1295               1300                1305

Asn Thr Asn Thr Gln Asp Pro Phe Leu Ile Gly Ser Ser Lys Gln
1310               1315                1320

Met Arg His Gln Ser Glu Ser Gln Gly Val Gly Leu Ser Asp Lys
1325               1330                1335

Glu Leu Val Ser Asp Asp Glu Glu Arg Gly Thr Gly Leu Glu Glu
1340               1345                1350

Asn Asn Gln Glu Glu Gln Ser Met Asp Ser Asn Leu Gly Glu Ala
1355               1360                1365

Ala Ser Gly Cys Glu Ser Glu Thr Ser Val Ser Glu Asp Cys Ser
1370               1375                1380

Gly Leu Ser Ser Gln Ser Asp Ile Leu Thr Thr Gln Gln Arg Asp
1385               1390                1395

Thr Met Gln His Asn Leu Ile Lys Leu Gln Gln Glu Met Ala Glu
```

-continued

|  | 1400 |  |  |  | 1405 |  |  |  | 1410 |  |  |
|---|---|---|---|---|---|---|---|---|---|---|---|

Leu Glu Ala Val Leu Glu Gln His Gly Ser Gln Pro Ser Asn Ser
1415                    1420                    1425

Tyr Pro Ser Ile Ile Ser Asp Ser Ser Ala Leu Glu Asp Leu Arg
1430                    1435                    1440

Asn Pro Glu Gln Ser Thr Ser Glu Lys Asp Ser His Ile His Gly
1445                    1450                    1455

Gln Arg Asn Asn Ser Met Phe Ser Lys Arg Pro Arg Glu His Ile
1460                    1465                    1470

Ser Val Leu Thr Ser Gln Lys Ser Ser Glu Tyr Pro Ile Ser Gln
1475                    1480                    1485

Asn Pro Glu Gly Leu Ser Ala Asp Lys Phe Glu Val Ser Ala Asp
1490                    1495                    1500

Ser Ser Thr Ser Lys Asn Lys Glu Pro Gly Val Glu Arg Ser Ser
1505                    1510                    1515

Pro Ser Lys Cys Pro Ser Leu Asp Asp Arg Trp Tyr Met His Ser
1520                    1525                    1530

Cys Ser Gly Ser Leu Gln Asn Arg Asn Tyr Pro Ser Gln Glu Glu
1535                    1540                    1545

Leu Ile Lys Val Val Asp Val Glu Glu Gln Gln Leu Glu Glu Ser
1550                    1555                    1560

Gly Pro His Asp Leu Thr Glu Thr Ser Tyr Leu Pro Arg Gln Asp
1565                    1570                    1575

Leu Glu Gly Thr Pro Tyr Leu Glu Ser Gly Ile Ser Leu Phe Ser
1580                    1585                    1590

Asp Asp Pro Glu Ser Asp Pro Ser Glu Asp Arg Ala Pro Glu Ser
1595                    1600                    1605

Ala Arg Val Gly Asn Ile Pro Ser Ser Thr Ser Ala Leu Lys Val
1610                    1615                    1620

Pro Gln Leu Lys Val Ala Glu Ser Ala Gln Ser Pro Ala Ala Ala
1625                    1630                    1635

His Thr Thr Asp Thr Ala Gly Tyr Asn Ala Met Glu Glu Ser Val
1640                    1645                    1650

Ser Arg Glu Lys Pro Glu Leu Thr Ala Ser Thr Glu Arg Val Asn
1655                    1660                    1665

Lys Arg Met Ser Met Val Val Ser Gly Leu Thr Pro Glu Glu Phe
1670                    1675                    1680

Met Leu Val Tyr Lys Phe Ala Arg Lys His His Ile Thr Leu Thr
1685                    1690                    1695

Asn Leu Ile Thr Glu Glu Thr Thr His Val Val Met Lys Thr Asp
1700                    1705                    1710

Ala Glu Phe Val Cys Glu Arg Thr Leu Lys Tyr Phe Leu Gly Ile
1715                    1720                    1725

Ala Gly Gly Lys Trp Val Val Ser Tyr Phe Trp Val Thr Gln Ser
1730                    1735                    1740

Ile Lys Glu Arg Lys Met Leu Asn Glu His Asp Phe Glu Val Arg
1745                    1750                    1755

Gly Asp Val Val Asn Gly Arg Asn His Gln Gly Pro Lys Arg Ala
1760                    1765                    1770

Arg Glu Ser Gln Asp Arg Lys Ile Phe Arg Gly Leu Glu Ile Cys
1775                    1780                    1785

Cys Tyr Gly Pro Phe Thr Asn Met Pro Thr Asp Gln Leu Glu Trp
1790                    1795                    1800

```
Met Val  Gln Leu Cys Gly Ala  Ser Val Val Lys Glu  Leu Ser Ser
1805                1810              1815

Phe Thr  Leu Gly Thr Gly Val  His Pro Ile Val Val  Val Gln Pro
1820                1825              1830

Asp Ala  Trp Thr Glu Asp Asn  Gly Phe His Ala Ile  Gly Gln Met
1835                1840              1845

Cys Glu  Ala Pro Val Val Thr  Arg Glu Trp Val Leu  Asp Ser Val
1850                1855              1860

Ala Leu  Tyr Gln Cys Gln Glu  Leu Asp Thr Tyr Leu  Ile Pro Gln
1865                1870              1875

Ile Pro  His Ser His Tyr
1880
```

METHODS AND SYSTEMS FOR IDENTIFICATION OF BIOMOLECULE SEQUENCE COEVOLUTION AND APPLICATIONS THEREOF

CROSS-REFERENCE TO RELATED APPLICATIONS

The current application claims priority to U.S. Provisional Patent Application Ser. No. 62/258,969 entitled "Methods And Systems For Identification Of Recurrently Mutated Functionally Related Protein Domains" to Colavin et al., filed Nov. 23, 2015, the disclosure of which is incorporated herein by reference as if set forth herein in its entirety.

STATEMENT REGARDING FEDERALLY SPONSORED RESEARCH OR DEVELOPMENT

This invention was made with Governmental support under contract GM107615 awarded by the National Institutes of Health. The Government has certain rights in the invention.

FIELD OF THE INVENTION

The invention is generally directed to methods and systems for identification and analysis of biomolecule sequence variation, and more specifically to methods and systems for identification of coevolving residues in biomolecules and applications thereof, which include the prediction of phenotypic impact of genetic variants on biomolecules.

BACKGROUND

Biomolecules—such as RNA, DNA, and proteins—carry out molecular functions through the coordinated activity and interaction of sub-networks of residues. During evolution, the sequences of biomolecules can accumulate changes that modulate the activity of these networks. Changes in the sequences of biomolecules are referred to as variants or mutations. For example, changes in the amino acid sequence of proteins often have profound effects on protein function, stability, or production leading to phenotypic variation. During molecular evolution, adaptive mutations that proffer an advantage are naturally selected and propagate, whereas mutations that are disadvantageous are selected against and eliminated from the population. Alternatively, mutations can have neither a positive or negative effect on fitness, yet may continue to propagate due to genetic drift.

In proteins, changes in amino acid sequence can be described as various types of mutations, including in-frame deletions, in-frame insertions, as well as frameshift, nonsense, and missense mutations. An insertion or deletion (indels) of amino acid residues can change the total number of amino acids resulting in a protein of a different size. Frameshift mutations arise when a nucleotide sequence incurs a loss or deletion of nucleotides that offset the triplet codon sequence, resulting in a completely different translation and amino acid composition. Nonsense mutations result in a premature stop codon, truncating the protein at the site of mutation. Missense mutations are point mutations having a single amino acid residue substitution. Although mutations are often tolerated and have negligible effects on proteins, mutations can have profound effects on the protein function, stability, and production, and are subject to yielding a wide array of clinical, therapeutic, pharmacokinetic, reproductive, developmental, behavioral, functional, nutritional, athletic, morphological, and aesthetic phenotypes.

An outstanding hurdle in applications of genetics to a wide array of problems is the prediction of the phenotypic effects of variants in biomolecules. For example, roughly 99.9% of possible single missense variants in human proteins have no established clinical phenotype. A promising avenue for improving the prediction of phenotypes conferred by biomolecular variants is to understand that position's role with the networks of residues that carry out molecular function related to the phenotype. One class of methods that could be used to reveal the network relationship between all residues in a protein is 'molecular coevolution', which measures the relationship between equivalent positions in biomolecules from homologous sequences. However, to date, coevolution methods are unable to distinguish between evolutionary relationships due to functional adaptation versus non-functional genetic drift. As a result, coevolution is unable to proffer insight into the functional relationships between positions, or act as the basis for accurate predictions of phenotypic effects of variants.

SUMMARY OF THE INVENTION

In many embodiments the invention is directed to methods and systems for identification of functionally-related residues in biomolecules and applications thereof. Herein, the embodiments presented demonstrate the methods claimed for the identification of functionally-related residues in biomolecules, and their application to identify and predict the phenotypic consequences of variants in biomolecules for the accurate interpretation of genetic tests.

In several embodiments, a computer-implemented method predicts function of unlabeled residue positions, wherein the method receives multiple sequence alignment data for a particular biomolecule using a computing system, wherein the multiple sequence alignment data comprises homologous sequences of the particular biomolecule;

computes a plurality of total covariation values of each pair of residue positions within the multiple sequence alignment data using the computing system;

defines at least two clades within the multiple sequence alignment data using the computing system based upon at least one phylogenetic cutoff,
  wherein each phylogenetic cutoff is defined by a phylogenetic distance, and
  wherein each clade is a group of sequences within the multiple sequence alignment data that have a phylogenetic distance equal to or below a particular phylogenetic cutoff;

computes inter-clade covariation values of each pair of residue positions within the multiple sequence alignment data for each particular phylogenetic cutoff using the computing system;

computes intra-clade covariation values of each pair of residue positions for each particular phylogenetic cutoff using the computing system;

builds an intra-clade covariation matrix describing the intra-clade covariation values of each pair of residue positions for each particular phylogenetic cutoff using the computing system, wherein the intra-clade covariation matrix comprises a matrix of intra-clade covariation values between residue positions for each particular phylogenetic cutoff;

builds a nested coevolution matrix that integrates signal from at least one intra-clade covariation matrix;

generates sector scores for each residue of the biomolecule sequence by applying a dimensionality reduction technique using the computing system;

identifies at least one biomolecule sector based on clustering of the generated coevolution sector scores, wherein the at least one biomolecule sector is a composite of coevolving residue positions of the particular biomolecule as identified by their sector scores;

links the identified at least one biomolecule sector with a set of residue positions of the particular biomolecule using the computing system, wherein at least one residue position within the set of residue positions has an assigned function as described by at least one dataset;

identifies at least one residue position having unlabeled function in the at least one biomolecule sector using the computing system, wherein the unlabeled function is to be predicted;

predicts at least one function for the residue positions having unlabeled function using the computing system, wherein the at least one predicted function is the function linked to the at least one identified biomolecule sector;

produces a report containing the at least one predicted function for the at least one residue positions previously having unlabeled function using the computing system;

and displays the report containing the at least one predicted function for the at least one residue positions previously having unlabeled function using the computing system.

In many embodiments, multiple phylogenetic cutoffs are used to build multiple matrices of intra-clade covariation values.

In other embodiments, the inter-clade covariation values are computed analytically or by bootstrapping.

In further embodiments, the phylogenetic distance is determined by the an evolutionary rate model, wherein the evolutionary rate model is as the Jukes-Cantor model, the Kimura model, the Felsenstein model, the Tamura model, the PAM model, the Jones model, the Whelman and Goldman model, the Dayhoff model, the Goldman model, the Felsenstein and Churchill model, the Goldman and Yang model, or the Muse and Gaut model.

In numerous embodiments, the dimensionality reduction technique generates eigenvectors based on an eigendecomposition of the nested coevolution values within the nested coevolution matrix using the computing system, wherein sector scores correspond to the eigenvectors and have associated eigenvalues determined by the eigendecomposition.

In more embodiments, the total covariation is calculated by the equation:

$$C_T^{i,j}=(H_i+H_j-H_{i,j})/H_{i,j}.$$

In several more embodiments, the dataset is a publicly or privately available database.

In many more embodiments, the biomolecule is a protein related to clinical phenotypes.

In numerous more embodiments, the dataset is a database of relationships between human genetic variants and clinical phenotypes.

In even more embodiments, the function is a clinical phenotype.

In even other embodiments, the method also receives sample sequence data of the particular biomolecule having at least one residue variant with unlabeled function using the computing system; and predicts a function of the at least one residue variant with unlabeled function that reside within residue positions of the linked at one biomolecule sector using the computing system, wherein the predicted function of the at least one residue variants with unlabeled function is the function linked to biomolecule sector.

In even further embodiments, the sample biomolecule sequence data is derived from a patient biopsy, a primary cell line, or an immortalized cell line.

In even several more embodiments, the method also builds a database of predicted residue position functions of residue variants previously having unlabeled function using the computing system.

In even many more embodiments, the method also ranks the sector scores using the computing system to identify biomolecule sectors having position residues that are highly coevolving.

In even further more embodiments, the intra-clade covariation values are computed by subtracting the inter-clade covariation value of each pair of residue positions from the total covariation value of each pair of residue positions using the computing system.

In several embodiments, a computer-implemented method for predicting phenotype of unlabeled residue positions with machine learning, wherein the method receives nested coevolution sector scores using a computing system, wherein the nested coevolution sector scores are generated by,
  receiving multiple sequence alignment data for a particular biomolecule using the computing system, wherein the multiple sequence alignment data comprises homologous sequences of the particular biomolecule;
  computing a plurality of total covariation values of each pair of residue positions within the multiple sequence alignment data using the computing system;
  defining at least two clades within the multiple sequence alignment data using the computing system based upon at least one phylogenetic cutoff,
    wherein each phylogenetic cutoff is defined by an phylogenetic distance, and
    wherein each clade is a group of sequences within the multiple sequence alignment data that have a phylogenetic distance equal to or below a particular phylogenetic cutoff;
  computing inter-clade covariation values of each pair of residue positions within the multiple sequence alignment data for each particular phylogenetic cutoff using the computing system;
  computing intra-clade covariation values of each pair of residue positions for each particular phylogenetic cutoff using the computing system;
  building an intra-clade covariation matrix describing the intra-clade covariation values of each pair of residue positions for each particular phylogenetic cutoff using the computing system, wherein the intra-clade covariation matrix comprises a matrix of intra-clade covariation values between residue positions for each particular phylogenetic cutoff;
  building a nested coevolution matrix that integrates signal from at least one intra-clade covariation matrix;
  generating coevolution sectors scores for each residue of the biomolecule sequence by applying a dimensionality reduction technique using the computing system;

receives sets of data describing residue variants labeled with a numerical or categorical label using the computing system, wherein the data describing the labeled residue variants comprises residue variants labeled as true positive for a phenotype and residue variants labeled as true negative for the phenotype;

assigns at least one feature to the labeled residue variants using the computing system, wherein the at least one feature comprises the nested coevolution sector scores;

trains a machine learning model on the set of labeled residue variants with at least one assigned feature using the computing system;

utilizes the machine learning model to predict the phenotype of at least one unlabeled variant within the particular biomolecule sequence using the computing system, wherein the phenotype is equated with the labeled phenotype of the true positive variants or the false positive variants;

produces a report containing the predicted phenotype of the at least one of unlabeled variant using the computing system; and displays the report containing the predicted phenotype of the at least one of unlabeled variant using the computing system.

In many embodiments, multiple phylogenetic cutoffs are used to build multiple matrices of intra-clade covariation values.

In other embodiments, the inter-clade covariation values are computed analytically or by bootstrapping.

In further embodiments, the phylogenetic distance is determined by the an evolutionary rate model, wherein the evolutionary rate model is as the Jukes-Cantor model, the Kimura model, the Felsenstein model, the Tamura model, the PAM model, the Jones model, the Whelman and Goldman model, the Dayhoff model, the Goldman model, the Felsenstein and Churchill model, the Goldman and Yang model, or the Muse and Gaut model.

In numerous embodiments, the dimensionality reduction technique generates eigenvectors based on an eigendecomposition of the nested coevolution values within the nested coevolution matrix using the computing system, wherein sector scores correspond to the eigenvectors and have associated eigenvalues determined by the eigendecomposition.

In more embodiments, the total covariation is calculated by the equation:

$$C_T^{i,j} = (H_i + H_j - H_{i,j})/H_{i,j}.$$

In several more embodiments, the dataset is a publicly or privately available database.

In many more embodiments, the biomolecule is a protein related to clinical phenotypes.

In numerous more embodiments, the dataset is a database of relationships between human genetic variants and clinical phenotypes.

In even more embodiments, the phenotype is a clinical phenotype.

In even other embodiments, the method also receives sample sequence data of the particular biomolecule having at least one residue variant with unlabeled function using the computing system; and predicts a phenotype of the at least one residue variant with unlabeled function that reside within residue positions of the linked at one biomolecule sector using the computing system, wherein the predicted phenotype of the at least one residue variants with unlabeled function is the function linked to biomolecule sector.

In even further embodiments, the sample biomolecule sequence data is derived from a patient biopsy, a metagenomic sample, a primary cell line, or an immortalized cell line.

In even several more embodiments, the method also builds a database of predicted residue position phenotypes of residue variants previously having unlabeled phenotype using the computing system.

In even many more embodiments, the machine learning model is Random Forests or Gradient Boosted Trees.

In even further more embodiments, the intra-clade covariation values are computed by subtracting the inter-clade covariation value of each pair of residue positions from the total covariation value of each pair of residue positions using the computing system.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention. The patent or application file contains at least one drawing executed in color. Copies of this patent or patent application publication with color drawing(s) will be provided by the Office upon request and payment of the necessary fee.

FIG. 1A illustrates a process for predicting structure and/or function of unlabeled residue variants in accordance with an embodiment of the invention

FIG. 2 illustrates a process for generating nested coevolution matrices in accordance with an embodiment of the invention.

FIG. 3 illustrates an example of multiple sequence alignment (MSA), which aligns SEQ ID NOs. 1-14.

FIG. 4 illustrates an example of a phylogenetic tree of a particular protein generated in accordance with various embodiments of the invention.

DETAILED DESCRIPTION

Figure 1B:
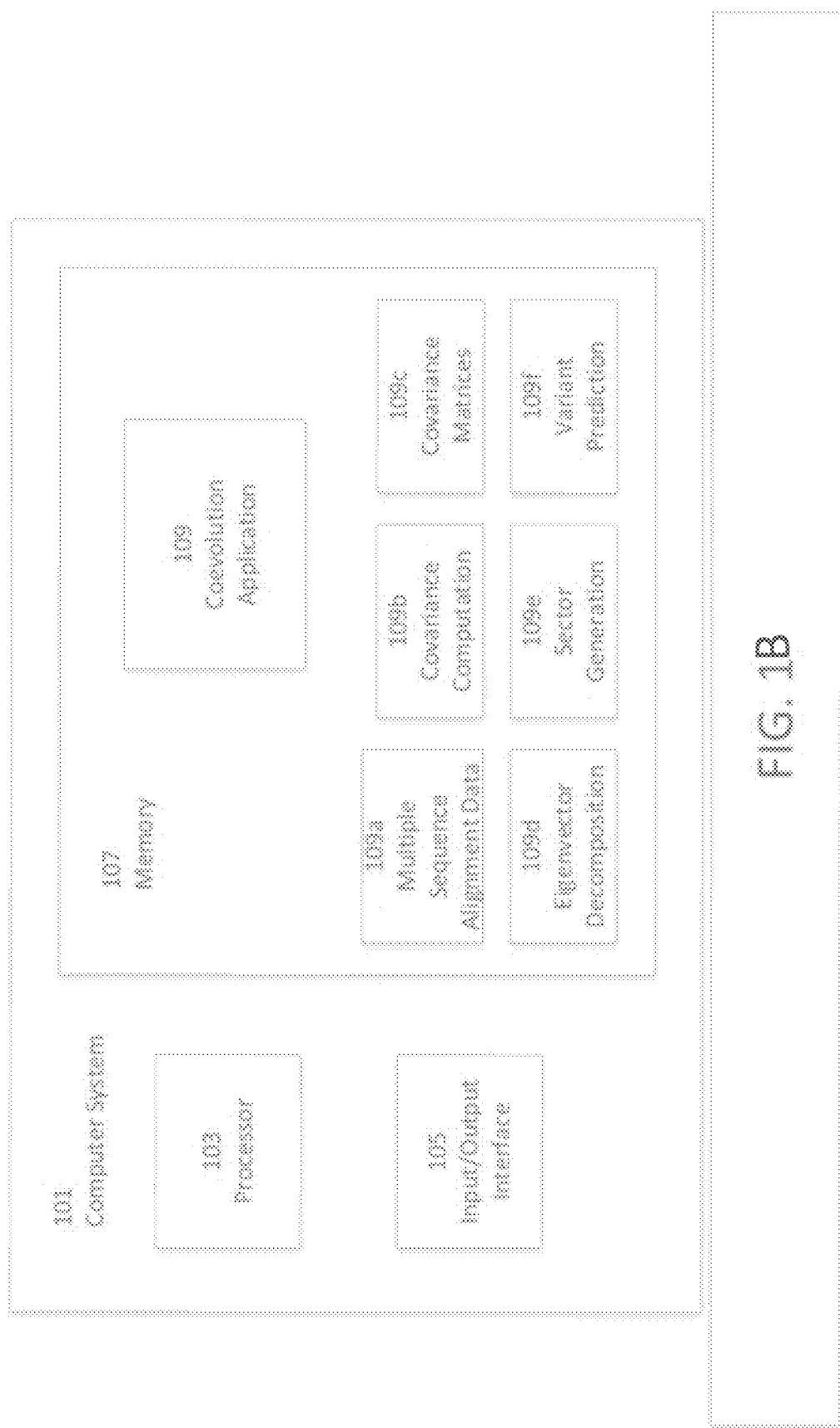
FIG. 1B illustrates a diagram of a computer system configured to identify biomolecule sectors of coevolving amino acid residue positions and to predict variant structure and/or function in accordance with various embodiments of the invention.

Turning now to the drawings and data, embodiments of the invention are generally directed to computational generation of sequence coevolution matrices that reveal residue positions coevolving in various evolutionary distances, and applying these signals to extract information of functionally-related residues that was previously indiscernible. In additional embodiments, the coevolution matrices can identify biomolecule sectors that are defined by groups of residues in a particular biomolecule that coevolve together within a particular evolutionary distance. More embodiments are directed to linking biomolecule sectors to a structure and/or function as determined by assigned, coevolving residue variants with a known structure and/or function. Additionally, a number of embodiments are directed to predicting the structure and/or function of unlabeled residue positions coevolving in the same sector as labeled variants. Many more embodiments of the present invention are directed at predicting the impact of genetic variants, including clinical phenotypes such as disease indications, by leveraging knowledge of functionally-related residues in machine learning models.

Accurately discerning coevolution between biomolecule residues and sectors that include coevolving pairs of residue positions has been a longstanding problem in the field that hitherto was unmet. This application, however, provides a solution that accurately discerns coevolution in multiple evolutionary distances, a feat that can only be performed by machine computation.

In several embodiments, the nested coevolution matrices are produced by determining the covariation of each pair of residue positions between the sequences within clades, which is a group of biomolecule sequences within an evolutionary distance. These evolutionary distances can be used to define a phylogenetic cutoff, such that the covariation between evolutionarily distant sequences can be removed. Because the inherent noise of phylogenetic drift is associated with more evolutionarily distant sequences, this noise may be removed from these covariation calculations. In more embodiments, this evolutionary distance parameter can be varied. To assist comprehension of the nested coevolution matrices, various embodiments are also directed to generating biomolecule sectors that identify groups of coevolving residue positions. Any dimensionality reduction and clustering method could work to identify biomolecule sectors, including, but not limited to, Mean Shift Clustering and Hierarchical Clustering. In some embodiments, generation of sectors scores computed as eigenvectors by eigendecomposition of the nested coevolution matrices can be performed to reduce the dimensionality of the nested coevolution matrix prior to clustering to identify biomolecule sectors. When sector scores are computed via eigendendecomposition, the resulting biomolecule sectors having high eigenvalues can be determined to have residue positions coevolving at a greater rate. Furthermore, the biomolecule sectors may also identify previously indiscernible functional and/or structural relationships between highly coevolving residues of the particular biomolecule.

Various methods in accordance with embodiments of the invention can be employed to generate matrices that reveal residue coevolution of particular biomolecules with covariation due to phylogenetic drift reduced. In several embodiments, a nested coevolution method is utilized that includes various combinations of processes and/or iterations to arrive at the desired matrices. These processes may include, but are not limited to:

- Alignment of multiple homologous sequences of a particular biomolecule to generate a multiple sequence alignment (MSA) for the biomolecule of interest
- Computation of the phylogenetic distances among the homologous sequences, which may be derived from the multiple sequence alignment (MSA) or from other sources of information (for example, a species-level phylogenetic tree)
- Computation of total covariation of each pair of residue positions of the particular biomolecule utilizing all sequences in the MSA
- Definition of clades of sequences within the multiple sequence alignment by their evolutionary distance such that a clade is a group of sequences within a particular evolutionary distance
- Computation of inter-clade covariation from each pair of residue positions utilizing sequences within distinct clades
- Computation of intra-clade covariation values, the covariation within clades, of each pair of residue positions of the particular biomolecule using the total covariation and the inter-clade covariation values
- Generation of intra-clade covariation matrices of each pair of residue positions of the particular biomolecule at specific evolutionary distances
- Computation of a nested coevolution matrix from a single or multiple intra-clade covariation matrices Methods in accordance with several embodiments of the invention can be employed to generate biomolecule sectors that include coevolving residue positions of a particular biomolecule. In several embodiments, a biomolecule sector identification method is utilized that includes various combinations of processes and/or iterations to linking biomolecule sectors with a structure and/or function. These processes may include, but are not limited to:

Retrieval of a nested coevolution matrix of a particular biomolecule

Generation of sector scores for each residue applying dimensionality reduction techniques such as, for example, the calculation of eigenvectors from the nested coevolution matrix Identification of biomolecule sectors from the sector scores such that the biomolecule sector is a group of amino acid residue positions coevolving together Association of specific biomolecule sectors with structural and/or functional relationships using known data on a residue position or residue variants that reside at positions within the biomolecule sector.

Methods in accordance with many embodiments of the invention can be employed to predict structure and/or function of residue positions and/or residue variants of a particular biomolecule. In several embodiments, a residue position prediction method is utilized that includes various combinations of processes and/or iterations to build variant function databases and/or report functions of variants within a sample. These processes may include, but are not limited to:

Retrieval of a particular biomolecule sequence having residue positions and/or residue variants with unknown structure and/or function Retrieval of function-associated biomolecule sector data of the particular biomolecule Prediction of structure and/or function of unlabeled residue positions and/or residue variants of unknown structure and/or function that reside within a function-associated sector using the linked structure and/or function of the biomolecule sector data Building a dataset of residue positions and/or variants with predicted structure and/or function Producing a report containing at least one prediction of structure and/or function of residue positions and/or residue variants on the basis of linked sector function Displaying the report containing at least one prediction of structure and/or function of unlabeled residue positions and/or residue variants with unknown structure and/or function Diagnosing samples having variants in the particular biomolecule sequence based on predicted structure and/or function of variants Methods in accordance with additional embodiments of the invention can be employed to improve the prediction of the phenotypic effects of variants. In several embodiments, machine learning models are trained to predict the phenotypic effects of variants. These methods include various combinations of processes and/or iterations to build better variant databases and/or better diagnose samples with variants. These processes may include, but are not limited to:

Receive sets of variants with associated phenotypic numerical or categorical labels, such as true positive and true negative variants, where true positive variants are known to have an attribute and true negative variants are known to lack that same attribute Assigning categorical and/or numerical features to labeled variants, such as nested coevolution sector scores based on each variant's position in the biomolecule, and other features such as biochemical, biophysical, functional, evolutionary, structural features of the variant Training a machine learning model on the set labeled variants Utilizing the machine learning model to predict the labels of variants, including those without a label Building a dataset of variants with assigned labels from the trained machine learning model Producing a report containing at least one label prediction of unlabeled variants Displaying the report containing at least one prediction of unlabeled variants Diagnosing samples from genetic tests through the assessment of variants in the sample using the predictions from the machine learning model trained on labeled variants It should be understood that a number of embodiments of the invention may include any combination of the above processes, but also encapsulate equivalent processes that could substitute any variety of the processes and still achieve substantially similar covariation matrices, biomolecule sectors, sector scores, and variant predictions.

Various embodiments of the invention are directed to the alignment of biomolecule sequences. In many of these embodiments, the sequences to be aligned are of a particular protein. It should be understood, however, that any adequate biological sequence, including DNA, RNA, and even lists of phenotypes could be aligned. Although protein sequences are described throughout, a person having ordinary skill in the art should know that samples having DNA, RNA, or lists of phenotypes can be aligned, coevolution computed, coevolution matrices produced, and function of residue positions predicted. This is particularly true for functional non-coding RNA sequences. Functional non-coding RNAs have no protein sequence to align and thus the sequence of RNA bases is responsible for its function. Computation of non-coding RNA coevolution would reveal sectors of the RNA sequence having coevolving base residues. The function of coevolving base residues can be predicted in the same methodology of coevolving amino acid residues as described throughout.

The number of sequences to be aligned can vary, and can be determined theoretically or empirically. For example, the sequences to be aligned might be within a certain evolutionary distance. Alternatively, the sequences to be aligned might share evolutionary, functional and/or clinical characteristics, or combinations thereof.

Several embodiments are directed to computing the nested coevolution values of each pair of residues of a particular biomolecule based on a multiple sequence alignment (MSA). In many embodiments, intra-clade coevolution values are generated as measures of the covariation between each pair of residues, removing noise associated with covariation attributed to phylogenetic drift. Thus, in many embodiments, nested intra-clade values are determined by calculating total covariation values and subtracting out the covariance due to inter-clade covariation, which can be depicted in the following equation:

$$C_{S \leq d}^{i,j} = C_T^{i,j} - C_{S>d}^{i,j}$$

In numerous embodiments, total covariation ($C_T$) is calculated between each pair of residues by any appropriate method, including Statistical Coupling Analysis (SCA), Direct Coupling Analysis (DCA), Mutual Information (MI), among many others. In some of the embodiments, the total covariation ($C_T$) is by a Normalized Mutual Information Metric, which calculates covariation between each residue position (i and j) by the following equation:

$$C_T^{i,j} = (H_i + H_j - H_{i,j})/H_{i,j},$$

where $H_i$ is the Shannon entropy of position i (a measure of conservation), and $H_{i,j}$ is the joint Shannon entropy between positions i and j (a measure of the coupling between residues). Shannon entropy can be calculated by the following equation:

$$H = \Sigma_a p_x(a) \log p_x(a)$$

where $p_x(a)$ is the probability of position X having residue identity a. These probabilities can be estimated for each position from an MSA.

In several embodiments, phylogenetic noise due to genetic drift may be removed. Removal of the phylogenetic noise involves delineation of clades of sequences of a particular biomolecule that are defined by a phylogenetic threshold. Accordingly, many embodiments of the method establish a phylogenetic cutoff that delineates sequences into clades close to one another in evolutionary distance. In further embodiments, the phylogenetic cutoff is varied, yielding different sets clades that vary in number of sequences.

The covariance due to phylogenetic drift, also referred to as inter-clade covariance ($C_{S>d}$), can be calculated by various methods. In some embodiments, the inter-clade covariation is determined analytically. In other embodiments, the inter-clade covariation is determined via bootstrapping. In some inter-clade covariations calculations, the analytical method is unavailable and thus bootstrapping should be performed. The availability of the analytical method is determined by the selected total covariation calculation, as some total covariation calculations cannot lend itself to a concrete equation to determine inter-clade covariation.

Intra-clade covariation is a signal of the differences of total covariation and inter-clade covariation. Thus, any method to signal this difference would fall under various embodiments of the invention. Methods to signal intra-clade covariation include, but are not limited to, subtracting inter-clade covariation from total covariation and calculating the probability of observing the total covariation value from the set of covariation values calculated from bootstrapped MSAs (p-value method). In various embodiments, intra-clade covariation values ($C_{S \leq d}$), can be calculated for each pair of residues of a particular biomolecule by subtracting the inter-clade covariation from the total covariation. In several embodiments, the calculated values can be built into nested coevolution matrices that depict the intra-clade covariation between each pair of residues. The matrices are modular, and can vary depending on the phylogenetic cutoff. Furthermore, the multiple intra-clade covariation matrices of multiple evolutionary distances can be built and layered into a single nested coevolution matrix when multiple phylogenetic cutoffs are used.

In more embodiments, biomolecule sectors of coevolving residue positions can be produced from sector scores, which describe the variance in the nested coevolution matrix in a reduced number of dimensions. Sectors scores can be computed through dimensionality reduction techniques such as eigendecomposition to yield eigenvectors of the nested coevolution matrices. The sector scores assign a value to each position in the biomolecule's sequence (i.e., each residue), and those positions with uniformly high or low relative values in specific sector scores can be grouped together to form a biomolecule sector. These sector scores can reveal biomolecule sectors of a particular biomolecule that are masked by the phylogenetic drift. In several embodiments, biomolecule sectors are composed of groups of residue positions of a particular biomolecule that are coevolving and functionally-related. These sectors may relate to known function or structure of a particular biomolecule, dependent on known data of residue positions within the biomolecule sector.

Numerous embodiments are also directed to prediction of residue position structure and/or function of a particular biomolecule. Residue positions with unknown structure or function may be identified in a biomolecule sequence sample. In many embodiments, when a residue position resides within a biomolecule sector relating to a structure or function, then the position's structure and/or function can be predicted. This prediction of residue positions can be extended to particular residue variants that exist within the residue positions of a biomolecule sector. The prediction data can be reported or stored in a dataset. Accordingly, embodiments are directed to reporting and/or building databases of residue positions with predicted function. Multiple embodiments are also directed to the ability of improving prediction of structure and/or function for an unlabeled variant structure or function by machine learning.

In many other embodiments, a biomolecule sector's function may be related to a pathogenic condition (e.g. hereditary cancer risk). Accordingly, variants that reside within that sector can yield insight on the pathogenicity or causality of that condition. For instance, sector scores may reveal enrichment of pathogenic or causal mutations in a biomolecule relevant to a disease state.

Overview of Nested Coevolution and Applications thereof

In accordance with several embodiments of the invention, systems and processes generate sequence coevolution matrices, sequence sectors, and residue position predictions. The generated matrices can be utilized to reveal information about biological sequence residues and their coevolution with one another. The coevolution matrices can also yield sequence sectors of highly coevolving residue positions. When the sequence sectors can be linked with a function, processes can predict the function of residue variants. These predictions can build databases of variant function or be used to diagnose a sample having sequences with particular variants.

The groups of sequences to be analyzed can be any biological sequence that has an evolutionary history. Accordingly, groups of DNA, RNA, or protein sequences can be analyzed for their coevolution. Matrices developed from their coevolution values can be further used to identify sectors and predict function of positions within the sequence. This analysis can also be applied to a sequence of phenotypes, in which the phenotypes are listed out in a linear fashion. Therefore, it should be understood that although the description throughout focuses on examples of protein sequence, other biological sequences can also captured by at least some of the embodiments of the invention.

In many embodiments, computer systems implement a robust method for explicitly separating the phylogenetic dimension of the coevolution signal, demonstrating that coevolution can occur on multiple phylogenetic distances within a single set of given sequences. Furthermore, highly evolving residues can have important roles in sequence function, which are validated in an exemplary embodiment that shows the functional capacity for such residues in eukaryotic actin. Coevolution in proteins like actin overlaps significantly with known missense mutations in known diseased states. For example, coevolution signals in oncoproteins overlap significantly with both frequent and rare somatic missense mutations that can accumulate in adapting neoplasms. The current conceptualization of the phylogenetic separation of coevolution represents a departure from previous attempts to reduce phylogenetic noise, and enables broad application of protein coevolution measurements, particularly to proteins with few homologs (e.g. many eukaryotic proteins), in a way that is compatible with a variety of existing methods of measuring coevolution.

Positional conservation is a common way to measure the relative importance of residues in a protein, since high evolutionary conservation of a position implies strong selection against mutations at that position. The relative conservation of a group of residues can be used to ascertain part of the protein behavior. For example, the functions of actin-family proteins have diverged across kingdoms (from MamK proteins which assemble magnetosomes, to ParM proteins involved in plasmid segregation during bacterial division), yet they all contain highly conserved ATPase motifs required to bind and hydrolyze nucleotide. From the presence of this motif in a sequence, one can predict part of its functionality.

Various embodiments of the invention are based upon a hypothesis that there is no a priori motivation for assuming that coevolution and conservation measure residue importance along the same dimension. Typically, residue coevolution and conservation have been treated as complementary measurements.

Turning now to FIG. 1A, a process for predicting the function of residue positions and residue variants is depicted as an embodiment of the invention. Process 100 can begin by computing the coevolution values for each residue position in a sequence (102). Coevolution, as will be described in detail below, is a measure of covariation of a group of sequences, also known as a clade. In accordance with many of embodiments of the invention, coevolution removes at least covariation that may be attributable to phylogenetic noise.

Process 100 can continue by using the computed covariation to build matrices that can be used to identify sectors of a sequence that are coevolving (104). A biomolecule sector, in accordance with several embodiments of the invention, is a cluster of residue positions of a given sequence that are found to coevolve with one another. Biomolecule sectors can be linked to a particular function when at least some of the coevolving residue positions within the biomolecule sector are described to have a particular function (106). Functions can be any be any biological or clinical phenotype, and thus can include, but not limited to, structure, enzymatic activity, biomolecule expression, biomolecule stability, pathogenicity, benignity, or disease onset.

Once sectors have been linked, residue positions and/or residue variants within the biomolecule sector with unknown or unlabeled function can be predicted to have the same function of the residue positions with known function (108). This prediction can extend to residue variants that reside within the residue positions. Furthermore, it is to be understood that unknown or unlabeled function includes any residue positions and/or residue variants in which the user wishes to predict the function. Thus, even though a residue may have a previously known or assigned function, if the user wishes to reassess and predict that function, it can do so in accordance with embodiments of this invention. This reassessment is especially true positions or variants with an assigned function that is either putative, low confidence, conflicted, or aberrant. The function prediction of residue positions and/or residue variants can be further improved and validated by machine learning (110).

Systems of Identifying Biomolecular Sequence Nested Coevolution

Turning now to FIG. 1B, a computer system (101) may be implemented on a single computing device in accordance with some embodiments of the invention. The computer system (101) may be a personal computer, a laptop computer, and/or any other computing device with sufficient processing power for the processes described herein. The computer system (101) includes a processor (103), which may refer to one or more devices within the computing device that can be configured to perform computations via machine readable instructions stored within a memory (107) of the computer system (101). The processor may include one or more microprocessors (CPUs), one or more graphics processing units (GPUs), and/or one or more digital signal processors (DSPs). According to other embodiments of the invention, the computer system may be implemented on multiple computers.

In a number of embodiments of the invention, the memory (107) may contain a nested coevolution processing program (109) that performs all or a portion of various methods according to embodiments of the invention described throughout the present application. As an example, processor (103) may perform the nested coevolution method (FIG. 2), during which memory (107) may be used to store various intermediate processing data such as the multiple sequence alignment data (109a), covariance computations (109b), the covariance matrices (109c), the sector scores (i.e. eigenvector decompositions) (109d), the biomolecule sectors generated (109e), and variant predictions (109f).

In some embodiments of the invention, the computer system (101) may include an input/output interface (105) that can be utilized to communicate with a variety of devices, including but not limited to a projector and/or other display devices. As can be readily appreciated, a variety of software architectures can be utilized to implement a computer system in accordance with several embodiments of the invention.

Although computer systems and processes for nested coevolution and performing actions based thereon are described above with respect to FIG. 1B, any of a variety of devices and processes for generating nested coevolution data structures, matrices, eigenvectors, and variant predictions as appropriate to the requirements of a specific application can be utilized in accordance with many embodiments of the invention. Below, processes for identifying biomolecule sequence coevolution and validation experiments based on embodiments of the invention are discussed.

Processes of Identifying Biomolecular Sequence Coevolution

In interrogate the contribution of phylogenetic sampling to biomolecule coevolution measurements, a number of embodiments of the invention separate the inter-clade and intra-clade covariation signal. The separation is performed because the inter-clade covariation can be a source of phylogenetic noise (e.g. the comparison of distantly related sequences). Processes for generating intra-clade covariation matrices with reduced phylogenetic noise in accordance with an embodiment of the invention are depicted in FIG. 2. Process 200 can begin with retrieving or developing a multiple sequence alignment (MSA) using homologous sequences for a biomolecule of interest (201). FIG. 3 depicts an example of an MSA. In this example, fourteen sequences of a particular protein are shown (Seq. ID Nos. 1-14); however, the number of sequences to be aligned can vary in accordance with the requirements of a given application. Likewise, in FIG. 4, the sequences of a particular protein to be aligned can be depicted in a phylogenetic tree, displaying their presumed genetic evolution, and the evolutionary distance between sequences.

The number of sequences within an MSA is to be determined either theoretically or empirically. For example, the sequences to be aligned might be within a certain phylogenetic distances (e.g., a Jukes-Cantor distance below 0.5). Alternatively, the sequences to be aligned might share an experimental or clinical characteristic (e.g., protein sequences derived from neoplastic patient samples). It should be understood that any suitable alignment program can be used to align the sequences of interest. Furthermore, routine alteration to MSA, such as, for example, pruning or removing redundancies, can be performed as necessary.

In many embodiments, the process 200 also involves measurements of the total covariations ($C_T$) (203) between every pair of positions using an established method. In some of these embodiments, total covariation can be computed by previously published methods, which include, but are not limited to, methods of Statistical Coupling Analysis (SCA), Direct Coupling Analysis (DCA), and Mutual Information (MI) (F. Morcos, et al., *Proceedings of the National Academy of Sciences*, 108, E1293-E1301 (2011); S. D. Dunn, L. M. Wahl, & G. B. Gloor, *Bioinformatics* (Oxford, England), 24(3), 333-40 (2008); N. Halabi, et al., *Cell*, 138(4), 774-86 (2009); references of which are incorporated herein by reference). In other embodiments, total covariation is calculated using the Normalized Mutual Information Metric of residue-residue coupling:

$$C_T^{i,j} = (H_i + H_j - H_{i,j})/H_{i,j},$$

where $H_i$ is the Shannon entropy of position i (a measure of conservation), and $H_{i,j}$ is the joint Shannon entropy between positions i and j (a measure of the coupling between residues). The calculated total covariation using the above equation has the special property of being conservation independent by virtue of the normalization by joint entropy.

In further embodiments, the process 200 defines clades of sequences (205). As described above, a MSA includes multiple homologous sequences of a particular biomolecule. These sequences can be divided into multiple clades based upon their phylogenetic distance to the particular biomolecule sequence (FIG. 4). As a representative example, in FIG. 4, clades of sequences of *Saccharomyces cerevisiae* actin are depicted in the different shaded boxes. The clades are dependent on their phylogenetic distance (d). Accordingly, some embodiments are directed to delineating sequences into a clade. A clade is a group of sequences having an evolutionary distance below a phylogenetic threshold, and thus all the sequences within a clade will be evolutionarily closer to one another than the sequences outside of the clade. Phylogenetic noise due to genetic drift associates more with evolutionary distant sequences.

The phylogenetic distance cutoff (d) that defines clades of sequences can be variable (FIG. 4). For example, FIG. 4 depicts a phylogenetic tree of *Saccharomyces cerevisiae* actin with four cutoffs ($d_1$-$d_4$) that define different clades of sequences. Accordingly, many embodiments are directed to defining clades of sequences by a phylogenetic distance that is variable. It should be understood that any suitable method to determine phylogenetic distance, such as the Jukes-Cantor model, the Kimura model, the Felsenstein model, Tamura model, the PAM model, the Jones model, the Whelman and Goldman model, the Dayhoff model, the Goldman model, the Felsenstein and Churchill model, the Goldman and Yang model, the Muse or Gaut model, can be used to establish a phylogenetic distance cutoff. Further, phylogenetic distances can be inferred from properties other than the MSA, such as the organismal phylogeny. It should also be noted that although the example in FIG. 4 depicts four cutoffs, the number of cutoffs can vary, and theoretically can be infinitely numerous. The specific cutoffs that are chosen typically depend upon the requirements of a given application. Calculating covariation on multiple phylogenetic cutoffs can enhance the generation of nested coevolution matrices and biomolecule sectors and reveal insights on coevolving residues on different evolutionary distances.

The number of clades can vary depending upon the phylogenetic distance cutoff (d). As shown in FIG. 4 as an example, cutoff d1 has eight individually defined clades, cutoff d2 has five defined clades, cutoff d3 has two defined clades, and cutoff d4 has one defined clade. Because of the variability of cutoffs, a particular MSA or phylogenetic tree can have multiple layers of defined clades. For example, when considering the phylogenetic tree of FIG. 4 as a whole, the multiple phylogenetic cutoffs $d_1$-$d_4$ yield layers of clades. Thus, some embodiments are specifically configured to generate a MSA or phylogenetic tree having multiple phylogenetic cutoffs that yield distinct definitions of clades.

Referring again to process 200, the process includes calculation of the inter-clade covariation ($C_{S>d}$) (207). In some embodiments, the expected values of inter-clade covariation is calculated either analytically or via bootstrapping. The choice of inter-clade covariation calculation will depend on the application to be performed. It should be understood that other inter-clade covariation calculations, in addition to analytical and bootstrapping, may appropriately fall within embodiments of the invention as described.

Bootstrapping is a method that can approximate the inter-clade covariation ($C_{S>d}$) (207). In this method, the original MSA of a particular biomolecule is bootstrapped, where every residue position is replaced with the identity of the same position from a random sequence in the same clade. For example, two positions are shown in the same clade below in Table 1, and separated by their clade membership. Notice that the left position is never a Serine in clade 1, or a Threonine in the clade 2. Similarly, the right position never has a Serine in the clade 1, or an Arginine in the clade 2. Thus, many bootstrapped MSAs are generated with the same phylogenetic structure of the MSA. By measuring the average covariation between the left and right positions for each bootstrapped MSA, the average statistical coupling between the positions should tend to values corresponding to zero covariation. The bootstrapping method can be conducted for any coevolution heuristic.

TABLE 1

Bootstrapping Method to Determine Inter-clade Expected Values

| | Raw MSA | Bootstrapped MSAs | | | | |
|---|---|---|---|---|---|---|
| Clade 1 | KD | TN | KD | TN | TD | KD |
| | KD | KN | KN | KD | KD | TD |
| | KD | KD | KD | KD | KN | KD |
| | TN | TN | KN | TD | TD | TD |
| Clade 2 | KD | QT | KD | KS | ND | QD |
| | KT | KS | KD | KT | KT | KS |
| | QS | NT | QS | QT | QS | NS |
| | NT | NT | NT | NT | ND | QD |
| | NT | QD | NS | ND | KT | NT |
| | NT | KS | ND | NT | KT | QT |
| | $C_T$ | $(C^1 + C^2 + C^3 + \ldots + C^n)/n = \langle C_{S>d} \rangle$ | | | | |

The analytical method is an analytical solution to replace bootstrapping. In various embodiments, the analytical method calculates the expected value of covariation between two positions under the assumption that the two positions are independent within a clade.

Consider the definition of Shannon entropy for position i.

$$H_i = \Sigma_j^{20} p_{i=j} \log p_{i=j}$$

The marginal probabilities of either position taking on a particular value do not change on average. However, the joint entropy, which relies on the joint probability, will change:

$$H_{i,j} = \Sigma_{k,l} p_{i=k,j=l} \log p_{i=k,j=l}$$

An expression for joint entropy can be formulated to capture the assumption that positions i and j are independent within clades. Since the joint probability of independent variables is the product of the individual probabilities, the sum of probabilities from each clade c can be calculated, and weighted by the number of sequences in each clade $n_c$.

$$p_{i=k,j=l}^{null} = \sum_c n_c p_{i=k}^c p_{j=l}^c$$

where $p_{i=k}^c$ is the marginal probability of position i taking identity k within clade c.

Figure 5:
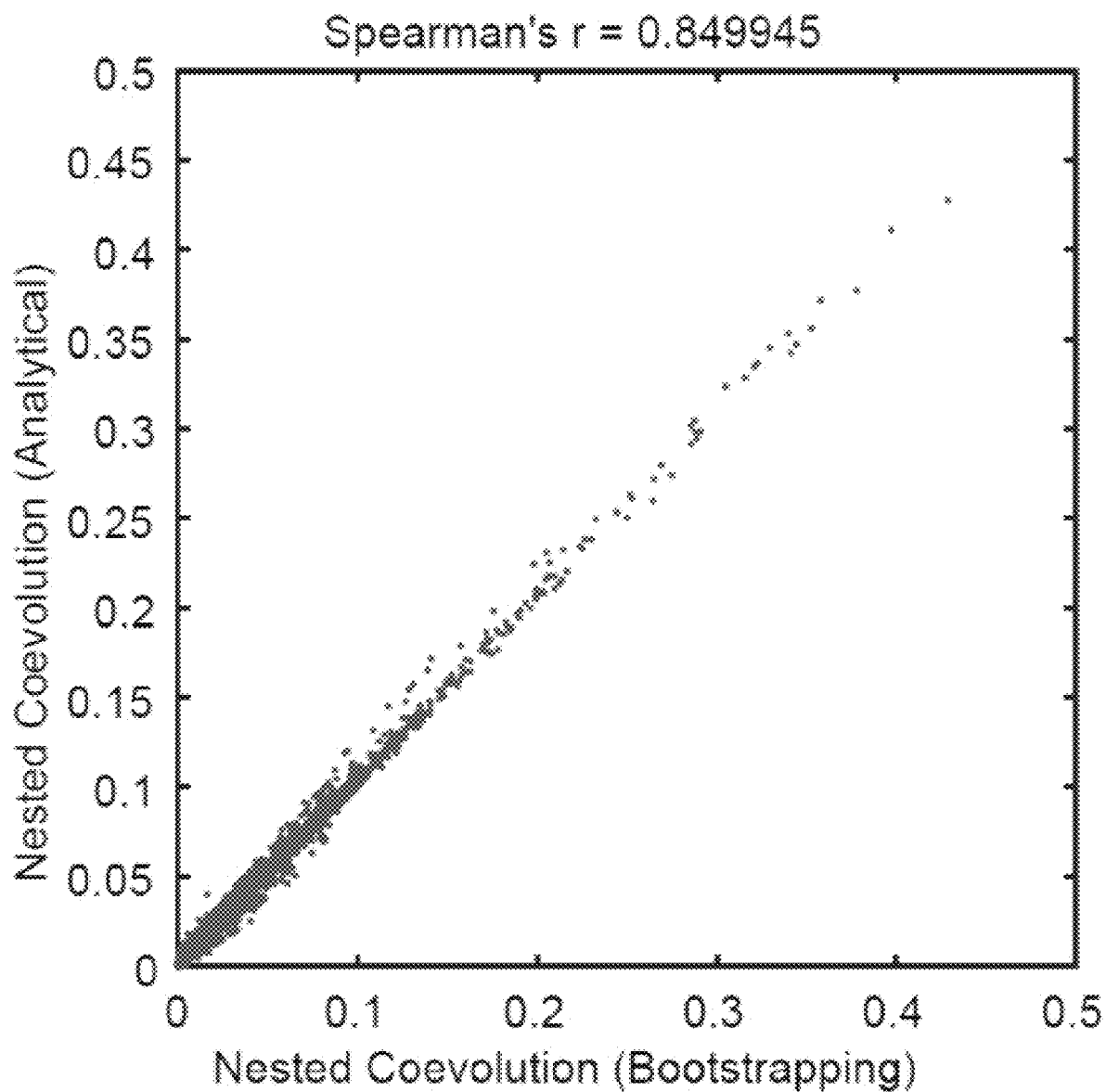
FIGS. 5 and 6 contrast nested coevolution calculations as determined by analytical and bootstrapping methods to calculate inter-clade covariation, generated in accordance with various embodiments of the invention.

An analytic solution is not always available for measuring the inter-clade covariation depending on the chosen metric of total covariation. In such a case, bootstrapping the MSA and averaging position values can be used to estimate the inter-clade covariation. A comparison of bootstrapped and analytical methods for calculating intra-clade covariation is shown in FIG. 5. In this example, in which the Normalized Mutual Information Metric was used to calculate total covariation, the inter-clade covariation at a particular value of phylogenetic distance was measured for every pair positions in Saccharomyces cerevisiae actin using either the analytical or bootstrapping method, plotted on the y and x axes respectively. Their agreement, demonstrated by the Spearman's correlation, indicates that the analytical and bootstrapping methods yield highly similar results.

Figure 6:
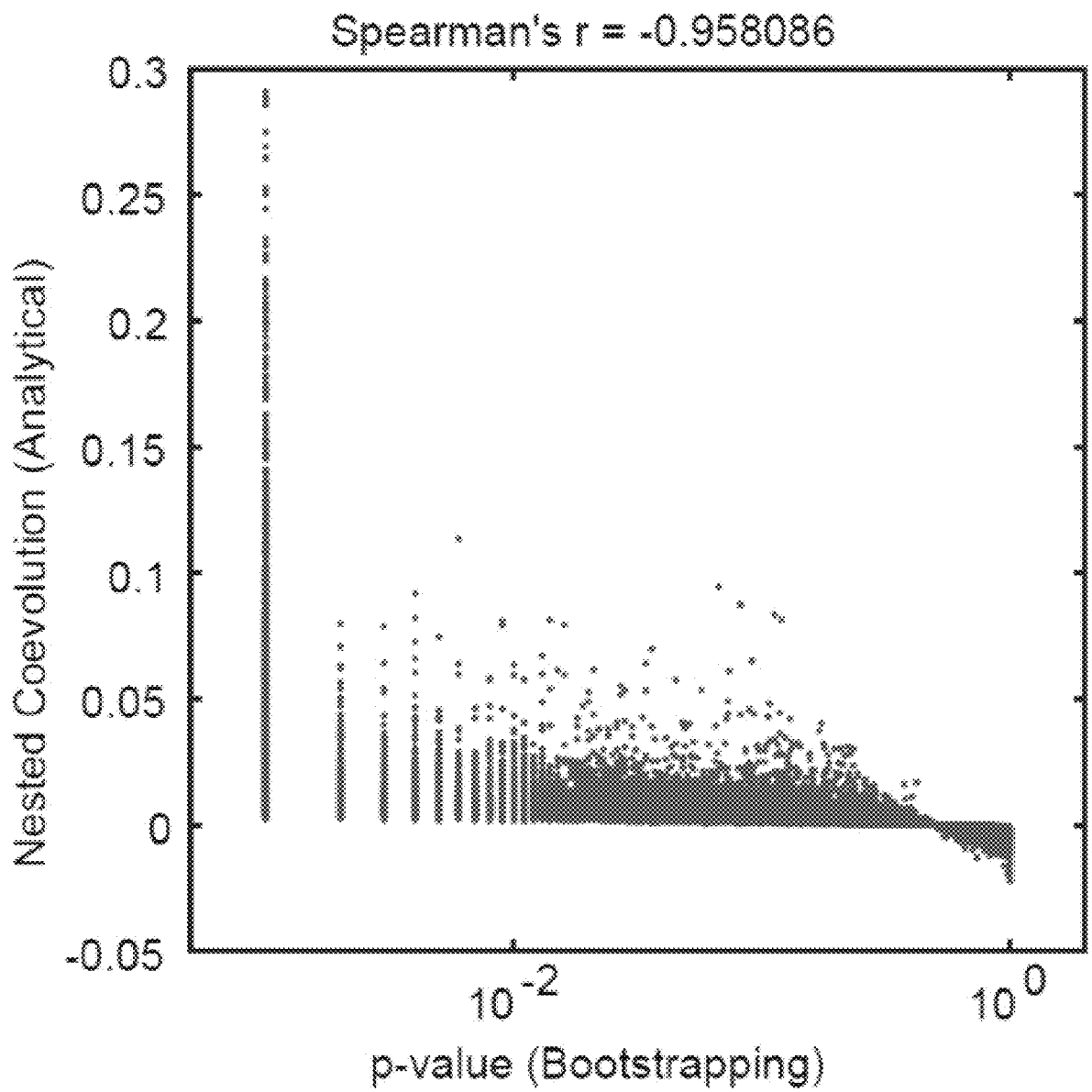

The analytical method to calculate inter-clade covariation is significantly less computationally expensive. The bootstrapped method, however, offers the advantage of calculating the probability of the null hypothesis that inter-clade covariation could account for the observed total covariation value. To determine whether the absolute difference between total and bootstrapped covariation values could be used as a surrogate for the significance of a given observation, the estimated significance of observation using the bootstrapped methods with absolute difference between the total and inter-clade covariation can be compared. It can be shown that a high degree of correspondence between these values (spearman's rho=0.95, FIG. 6), confirming that it is possible to recover a surrogate for the significance of the observation using the analytical method alone.

Several embodiments of Process 200 compute intra-clade covariation values ($C_{S \leq d}$) for each pair of residue positions of a particular biomolecule sequence (209). In many of these embodiments, the intra-clade covariation is determined by subtracting the inter-clade covariation ($C_{S>d}$) from the total covariation:

$$C_{S \leq d}^{i,j} \equiv C_T^{i,j} - C_{S>d}^{i,j}$$

This calculation separates the covariation signal due to comparison of sequences either within or between clades of a phylogenetic tree. Positive values indicate that the inter-clade covariation is insufficient to account for the total covariation. Accordingly, various embodiments are directed to clade determinations that have the inter-clade covariation removed.

Figure 7:
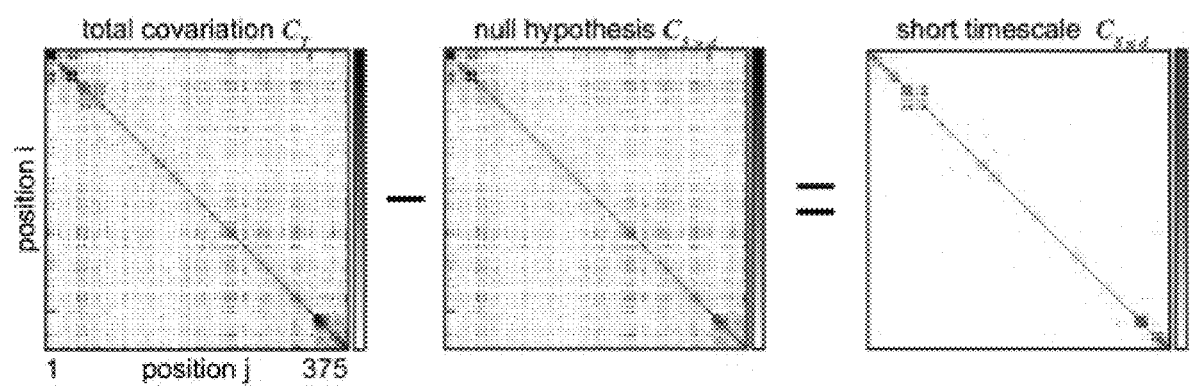
FIG. 7 illustrates examples of total covariation, inter-clade covariation, and intra-clade covariation matrices generated in accordance with various embodiments of the invention.

Process 200 also generates intra-clade covariation matrices and computes a nested coevolution matrix (211). These matrices describe the intra-clade covariation values that are calculated for each residue position pair within a particular biomolecule. These generated matrices depict the level of covariation between each residue pair at a selected evolutionary distance. The computation of intra-clade covariation can be repeated for every evolutionary distance selected (213). As a representative example, FIG. 7 depicts covariance matrices of Saccharomyces cerevisiae actin using the phylogenetic cutoff of $d_1$ (FIG. 4). The left panel of FIG. 7 is the total covariance ($C_T$) matrix, as calculated using $C_T$ calculation as described above. The middle panel is null hypothesis, or the inter-clade variation ($C_{S>d}$) as determined in this example by the analytical method. The right panel is the intra-clade covariation ($C_{S \leq d}$) values of S. cerevisiae actin of similar homologous sequences as defined by the phylogenetic cutoff $d_1$. The intra-clade covariation matrix is determined by subtracting the inter-clade covariation matrix from the total covariation matrix.

The intra-clade covariation matrix ($C_{S \leq d}$) reveals which residue pairs evolve together. As depicted in FIG. 7, the darker shading indicates higher levels of covariation. Accordingly, FIG. 7 depicts that various pockets of residues along the actin peptide chain have strong covariation signals with each other. Interestingly, at least in this example of S. cerevisiae actin, covariation of N-terminal residue positions is strong with other nearby N-terminal positions, and covariation of C-terminal positions is strong with other nearby C-terminal positions, but covariation of N-terminal positions with C-terminal positions is relatively weak. This particular matrix suggests that covariation of S. cerevisiae actin occurs within similar protein domains of contiguous residues.

Figure 8A:
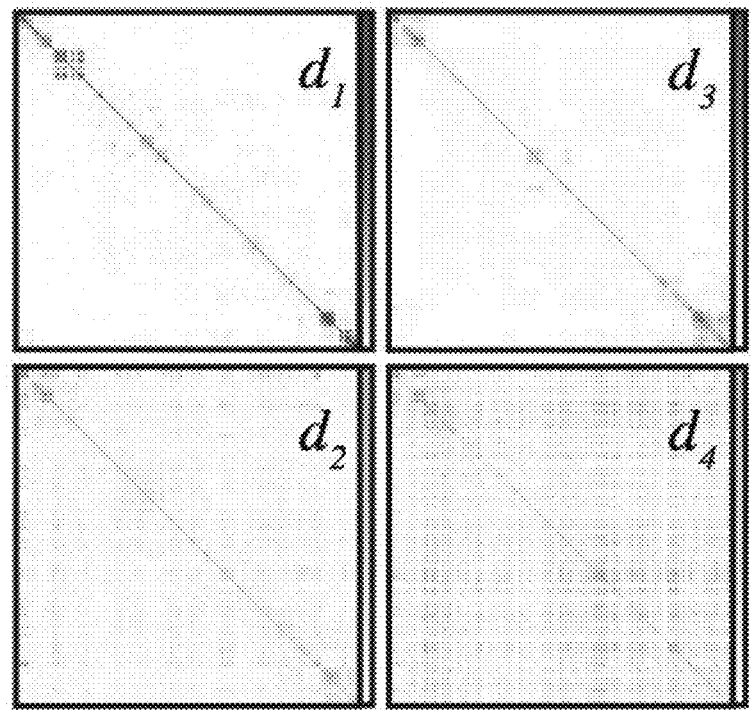
FIG. 8 illustrates an example of multiple intra-clade covariation matrices with different phylogenetic distance cutoffs generated in accordance with various embodiments of the invention.
Figure 8B:
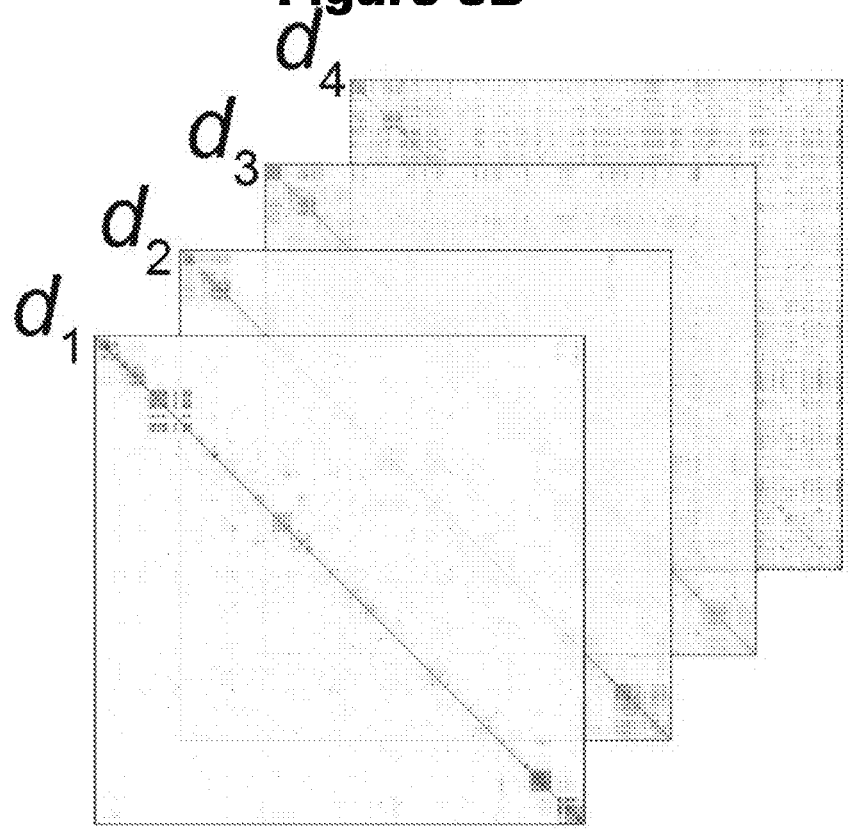

As mentioned above, the phylogenetic distance cutoffs (d) can vary (FIG. 4). In this particular S. cerevisiae actin example, phylogenetic distance cutoffs were chosen by evenly sampling four values between the minimum and maximum phylogenetic distances found between the sequences in the alignment. Although four cutoffs are depicted in this example, it should be understood that the number of cutoffs can vary depending on the application. The chosen phylogenetic distance cutoffs ($d_1$-$d_4$) resulted in four distinct matrices that combined together build a nested coevolution matrix that integrates signal from each of the four matrices (FIG. 8). As can be seen, the shorter the phylogenetic distance cutoff, the less signal noise results, due to the reduction of phylogenetic noise. Furthermore, these matrices can be stacked upon one another, generating layered data structures of different evolutionary distances that reveal at which phylogenetic distance the resultant covariation signal can be attributed to (FIG. 8B). Accordingly, various embodiments are directed to generation of nested coevolution matrices of different evolutionary distances that describe the intra-clade covariation between pairs of residue positions at various phylogenetic distance cutoffs.

Figure 9:
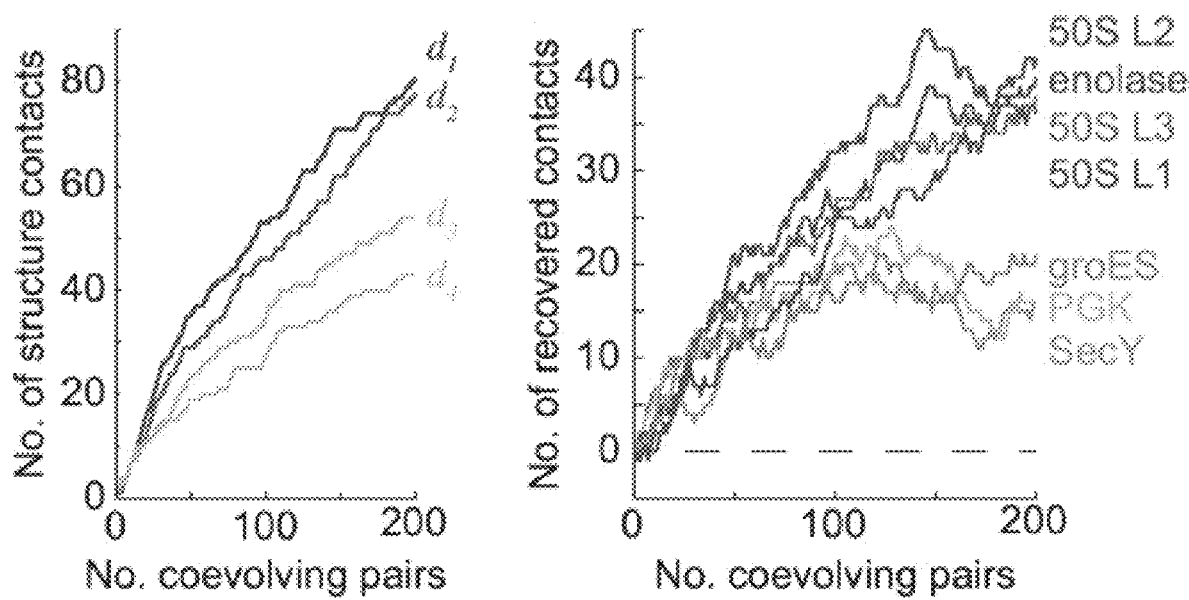
FIG. 9 illustrates two graphs detailing coevolving pairs of residues in multiple phylogenetic distances and in multiple protein homologs generated in accordance with various embodiments of the invention.

Using the representative S. cerevisiae actin example, the matrices show by varying the phylogenetic distance (d), the protein's intra-clade covariation generally changed substantially. For large phylogenetic cutoffs, covariation between residues spanned the entire protein. This signal resembled the background signal in the total covariation (FIG. 8A, box $d_4$, compared to FIG. 7, left panel), suggesting that the phylogenetic contribution to covariation occurs due to the comparison of distantly related sequences. For intermediate cutoffs, clusters of coevolving residues emerged with very little background signal (FIG. 8A, boxes $d_2$, $d_3$). Strong intra-clade covariation was detected even with small phylogenetic cutoffs (FIG. 8A, box d₁), for which signal can arise only from correlated changes between residues that differ in otherwise highly similar sequences. Intra-clade covariation measurements at lower phylogenetic cutoffs can be enriched for structurally proximal contacts (FIG. 9, left panel). These findings were consistent across a range of proteins highly conserved across all kingdoms of life (FIG. 9, right panel).

Processes of Biomolecule Sector Identification and Variant Prediction

Several embodiments of the invention are directed to decomposition of the constructed nested coevolution matrices into sector scores and biomolecule sectors. In many of these embodiments, the dimensionality reduction techniques such as eigendecomposition are deployed to yield sector scores, which describe the variance in the nested coevolution matrix in a reduced dimensionality. Sectors scores can be used to grouped together residues to form a biomolecule sector, a set of residue positions that are coevolving together. In some embodiments, various sectors relate to a function. When the biomolecule sectors include positions that are correlated with databases of known function, the biomolecule structures can predict structure or function of other residue variants in a particular biomolecule sequence. In many embodiments, the variant prediction methods are improved by machine learning and classification or regression model training. Embodiments of these predictive models are more accurate and outperform untrained predictions. Furthermore, in several of these embodiments, the known biomolecule function is related to the phenotype of a certain category. In more specific embodiments, the category is oncogenesis, tumorigenesis, carcinogenesis, drug sensitivity, cancer susceptibility, disease carrier, prenatal testing, newborn screening, or research genetic testing.

Figure 10:
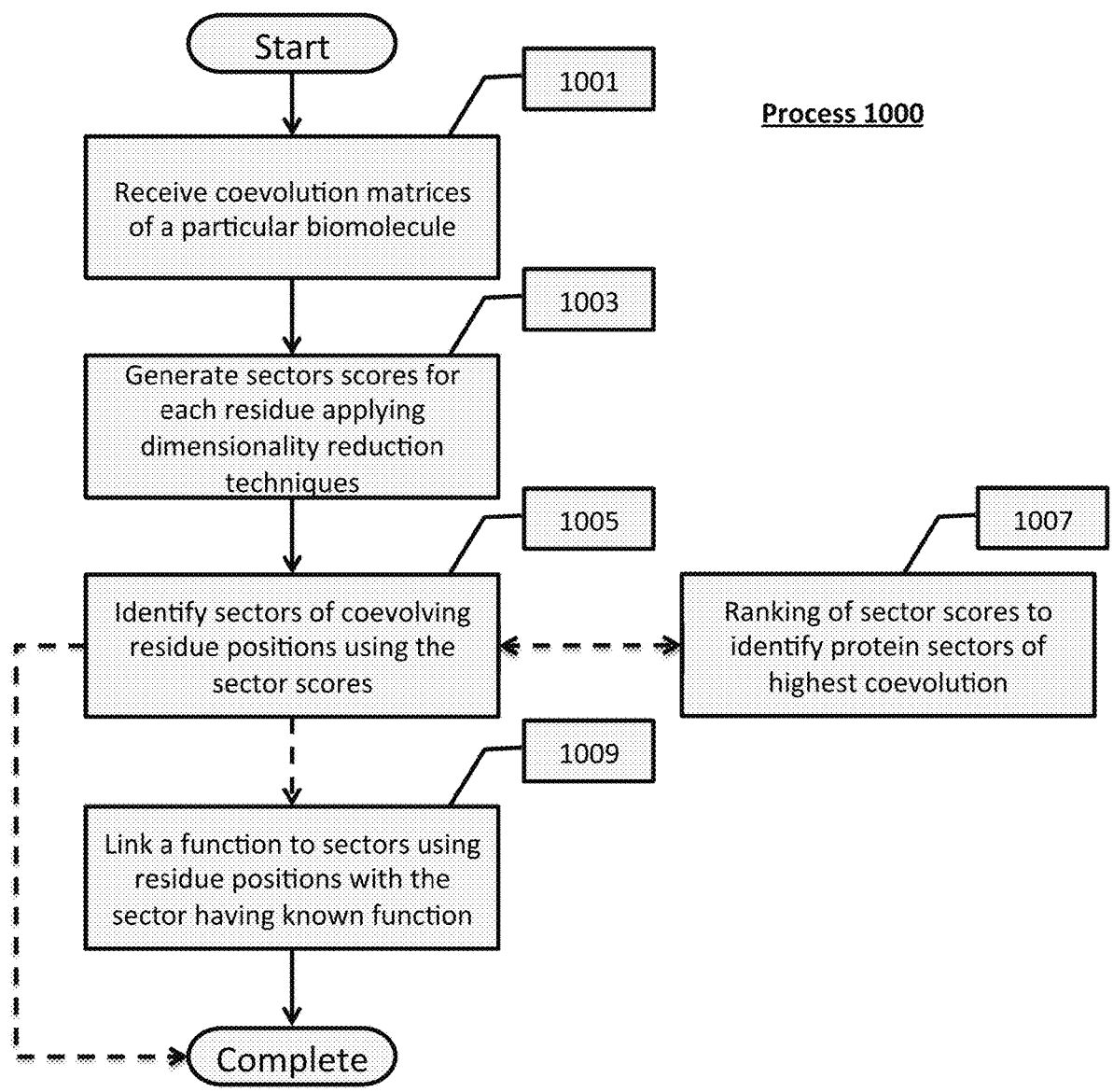
FIG. 10 illustrates a process for identifying and linking biomolecule sectors in accordance with an embodiment of the invention.

In numerous embodiments, dimensionality reduction (e.g., eigenvector decomposition) and clustering can reveal biomolecule sectors of a particular biomolecule sequence constituting residue positions that coevolve together with other residue positions. Furthermore, the dimensionality reduction and clustering can reveal sectors having a related structure, function, or interaction. An embodiment to decompose the nested coevolution matrices into biomolecule sectors is depicted in FIG. 10. Although eigendecomposition and generation of eigenvectors is depicted and described, it should be understood that any appropriate dimensionality reduction and clustering methods could be incorporated for calculating sector scores and biomolecule sectors. For example, other clustering methods include Mean Shift Clustering and Hierarchical Clustering (D. Comaniciu, P. Meer & S. Member, IEEE, 24(5), 603-619 (2002); J. Dutheil & N. Gatlier, BMC Evolutionary Biology, 7 (November), 242 (2007); the disclosures of which are incorporated herein by reference).

Process 1000 can begin with retrieving intra-clade covariation matrices for a biomolecule of interest (1001). The matrices can be built by process 200 (FIG. 2), as described above, or another process that adequately yields nested coevolution matrix. Likewise, the retrieved intra-clade covariation matrices can be layered, having nested coevolution data on multiple evolutionary distances. Accordingly, many embodiments are directed to retrieval of intra-clade covariation matrices of a particular biomolecule on at least one evolutionary distance.

Process 1000 can generate sector scores for each residue applying dimensionality reduction techniques (1003). In one such technique, nested coevolution are generated eigenvectors by decomposing the retrieved nested coevolution data structures and matrices. For example, using a MSA of a particular protein, intra-clade covariation can be measured for various phylogenetic cutoffs ($d_1$-$d_n$) and linearly sampled from to the smallest and largest distance that occurs between all pairs of sequences. This matrix can be manipulated into a p by (p×n) matrix, where p is the length of the protein sequence, and n is the number of matrices generated by unique phylogenetic distances, and where every row captures the coevolution of a protein position with every other position on multiple phylogenetic distances. Empirically, phylogenetic signals dominate covariation signals. To remove these signals, principal component analysis (PCA) can be used to reconstruct the matrix with all eigenvectors except the most prominent eigenvector, as determined by the largest absolute eigenvalue. Importantly, these eigenvectors should not be confused for eigenvectors used to determine sectors. Finally, the last p columns of this reconstructed p×(p×n) matrix determines a form of a nested coevolution matrix. Eigendecomposition and other dimensionality reduction techniques can be applied to this matrix to determine sectors scores, and groups of coevolving residues (i.e. biomolecule sectors).

Process 1000 can also identify sectors that exhibit intra-clade covariation on multiple evolutionary distances using the sector scores (e.g. eigenvectors) (1005). Furthermore, the sector scores can be ranked to identify biomolecule sectors of highest coevolution (1007). For example, after decomposition, eigenvectors can be ranked according to their respective eigenvalues, and the eigenvectors that yield high eigenvalues can reveal coevolution sectors of highly coevolving residues. These sectors relate to various residue positions within a biomolecule of interest, wherein the various residue positions are found to all have high sector score values. Biomolecule sector composition is determined analytically on the basis of nested coevolution values without bias toward already known biomolecule sequence information or function. Because of this lack of bias, sectors reveal a priori knowledge concerning coevolving residues that are likely to be undiscoverable by previous methods of biomolecule sequence covariation and conservation. Accordingly, many embodiments are directed to a priori identification of biomolecule sectors composed of various residue positions that are not biased toward known sequence information or function.

Because dimensionality reduction and clustering of nested coevolution matrices reveals biomolecule sectors of unbiased composition, the identified sectors may be composed of virtually any set of residue positions of a particular biomolecule, as determined by their coevolution. Biomolecule sectors may be composed of coevolving residue positions that are contiguous or disparately spaced along the peptide chain. As such, sectors may be composed of precisely one biomolecule domain, partial domains, or multiple domains. Biomolecule sectors may also be composed of a few residue positions, or of many positions. As such, sector composition of residue positions will vary, depending on which residues coevolve together within a particular evolutionary distance or set of distances.

Referring back to Process 1000, the process can link the identified sectors with a function, as determined from residue positions described to have a function from a publicly or privately available database (1009). Once a biomolecule sector has been identified, the composition of residue positions may correlate with known sequence information of the biomolecule of interest. For example, if residue positions within the biomolecule sector are known to contribute to a particular function or structure, that linkage would reveal that the particular function or structures is coevolving. It should be noted that any suitable public or private database could be used, for example, National Center for Biotechnology Information (NCBI)'s ClinVar or The Human Gene Mutation Database (HMGD). It should be understood that any database that maintains relationships between human genetic variants and clinical phenotypes could be used, and fall within various embodiments of the invention. Other examples of databases that could be used include genome-wide databases of disease-associated variants such as Online Mendelian Inheritance in Man (OMIM), Universal Mutation Database (UMD), and Diagnostic Mutation Database (DMuDB), locus-specific databases such as the BRCA Challenge and Clinical and Functional Translation of CFTR (CFTR2), disease-specific databases such as the Type-2 Diabetes Knowledge Portal (T2D Knowledge Portal) and the Clinical Interpretations of Variants in Cancer (CIViC) database, pharmacogenomics-focused databases such as the Pharmacogenomics Mutation Database (PGMD) and the Pharmacogenomics Genome Knowledgebase (PharmGKB), among other databases.

The linkage of biomolecule sectors to a particular function or structure depends on the known knowledge of residue variants that lie within residue positions of the biomolecule sector. This knowledge often exists in publicly or privately available variant databases that relate known variants to known functions and structures. Thus, description of a biomolecule sector depends on its residue position composition, known variants that reside within these positions, and knowledge of altered function related to the residue position or known variants. Accordingly, sectors may relate to particular alterations of function or structure. For example, a biomolecule sector may relate to the pathogenicity of a disease state. Some sectors may be innocuous, and not involved in pathogenicity of a disease state, and instead exhibit coevolution due to evolutionary selective pressure independent of the mechanism of action for a given disease state.

Figure 11:
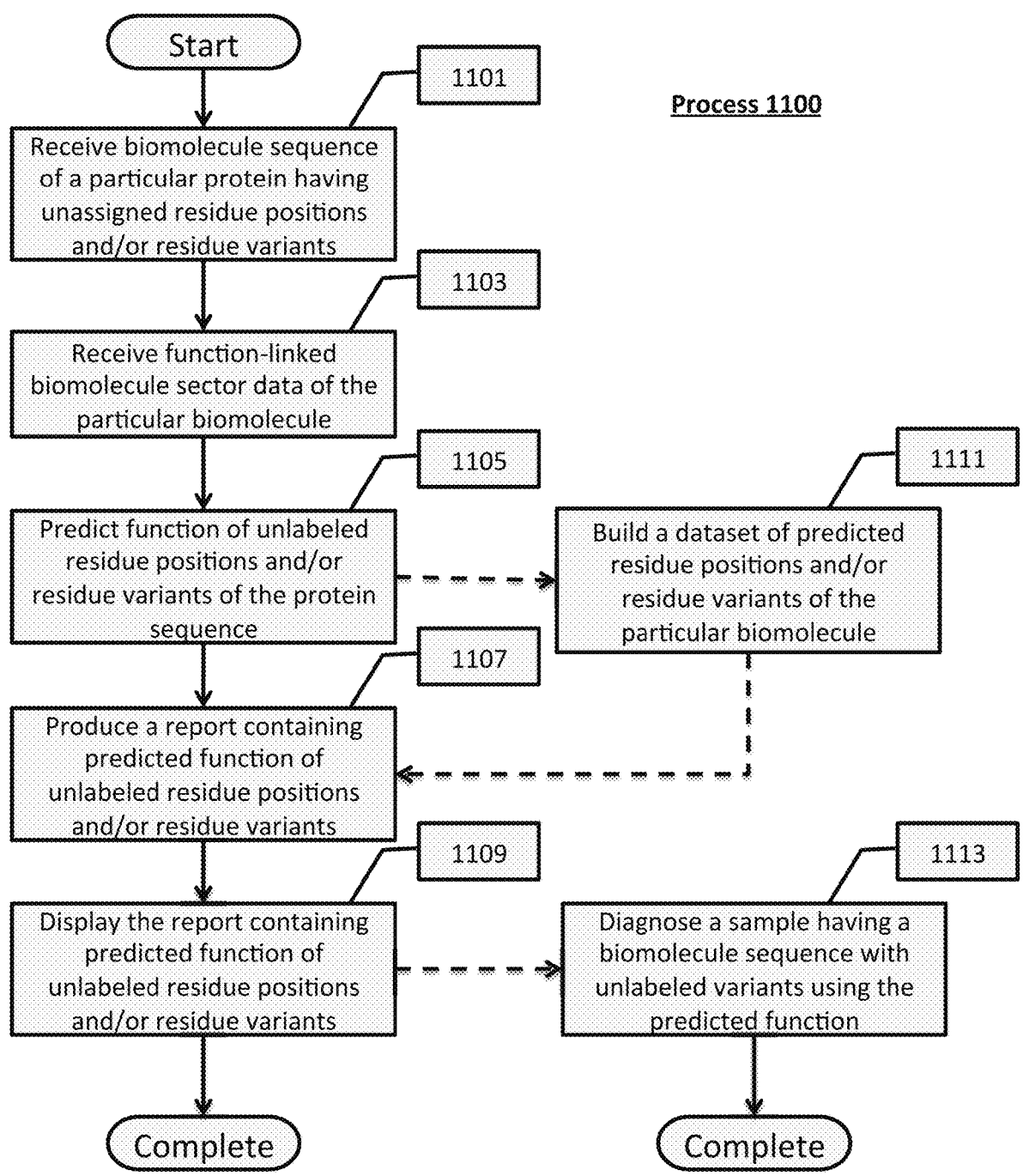
FIG. 11 illustrates a process for predicting structure and/or function of unlabeled residue variants in a sample in accordance with an embodiment of the invention.

Biomolecule sector linkage with databases can also predict knowledge about unlabeled residue positions and/or variants of the biomolecule of interest within a particular sector (FIG. 11). Because some residue variants are rare and other variants have not been assigned to particular functionality or structure within a database, if a rare or unlabeled variant of particular biomolecule is identified within a linked sector, it is possible to predict the rare or unlabeled variant's altered function or structure. For example, a particular biomolecule sequence may have a rare mutation. If this mutation is unlabeled in known databases of variant pathogenicity, simple comparison with these databases will reveal no knowledge about this mutation's pathogenicity. However, if this mutation is found to lie within an identified coevolving sector that is linked to known pathogenicity, this knowledge predicts that is likely that this mutation contributes to the pathogenesis of a disease state. Thus, sectors that can be linked to a known function or structure expand the ability to predict the contribution of unlabeled residue positions and/or mutations. Accordingly, several embodiments are directed to revealing new knowledge of rare or unlabeled residue positions and/or sequence variants, as determined by linked biomolecule sectors.

FIG. 11 depicts an embodiment, Process 1100, which is able to link unlabeled residue variants of a particular biomolecule to identified and linked sectors. To begin, Process 1100 can receive biomolecule sequences having unlabeled residue variants (1101). As mentioned previously, an unlabeled variant is simply a variant that a user wishes to predict. These biomolecule sequences can be a sequence within the MSA or derived from any sample source, including cell lines, a metagenomic sample biopsies, bacteria, viruses, or any other biological tissue. Furthermore, the biomolecule sequence data can be acquired by any suitable method, including by genomic sequencing, RNA sequencing, protein sequencing, or from a sequence database.

Process 1100 can receive linked biomolecule sector data of a biomolecule of interest, wherein the biomolecule sector is linked to a known function or structure (1103). Methods to link biomolecule sector to known functions or structures are above, but any suitable data of linked biomolecule sectors can be used. As described above, sectors can be linked to any known function or structure, as can be identified with known variants found within the biomolecule sector.

Process 1100 can also predict the function associated with unlabeled residue positions and/or variants of the biomolecule sequence, in accordance with linked sectors of which the unlabeled residue positions and/or variants positions reside within (1105). Furthermore, using the predicted functions of residues, a dataset and/or databases can be built, consolidating the predicted function data (1111). A report containing the data of the predicted functions, whether in dataset form or individually, can be produced (1107) and displayed (1109). This data can further be used to diagnose a sample having a variant with function predicted by the biomolecule sector data (1113). The sample may be derived from any appropriate biological source, including, cell lines, patient biopsies, bacteria, viruses, or any other biological tissue.

Figure 12:
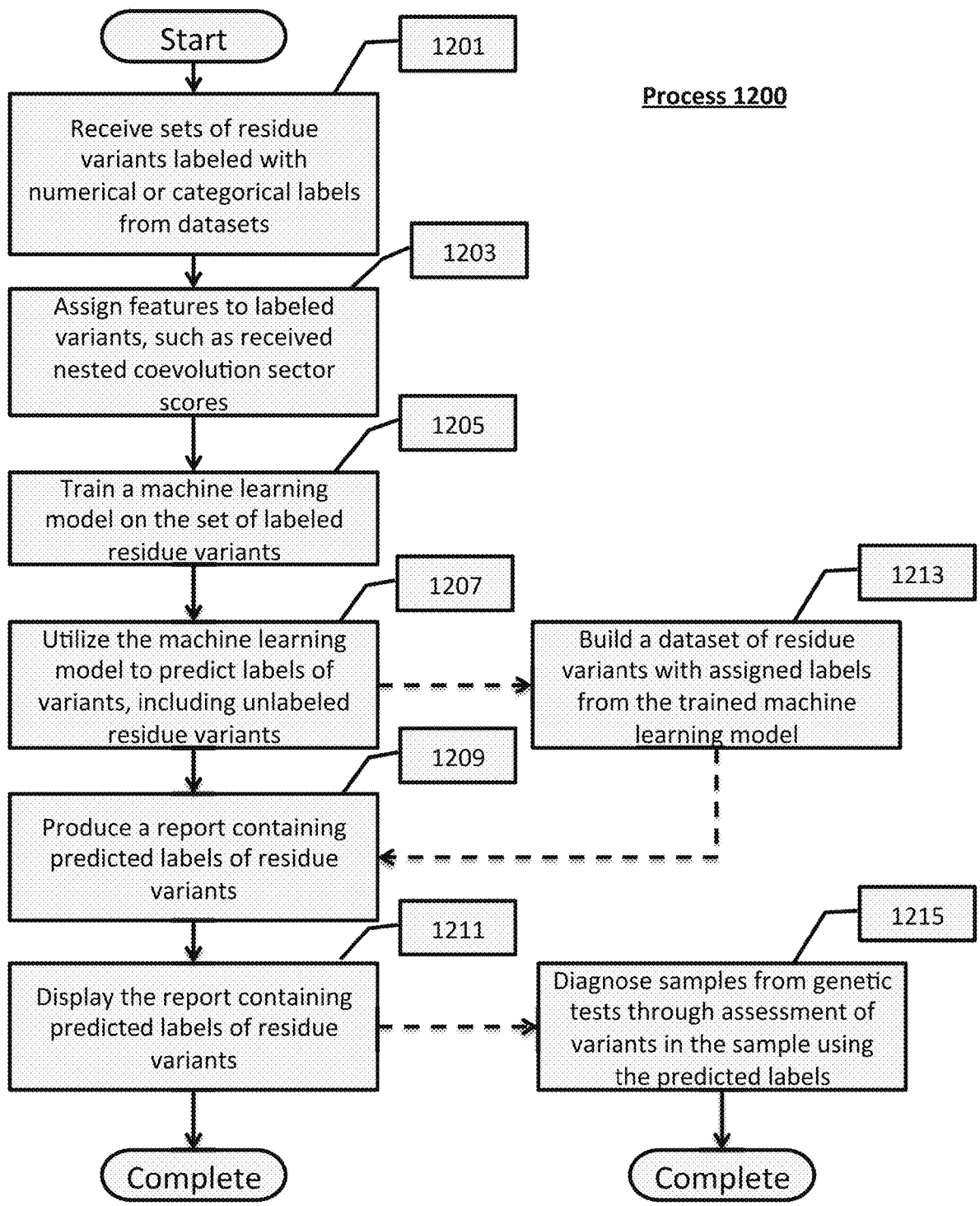
FIG. 12 illustrates a process that utilizes machine learning to enhance prediction of structure and/or function of unlabeled residue variants in accordance with an embodiment of the invention.

Applied genetics and genetic testing involves diagnosis, management, and determination of the propensity for diverse phenotypes with hereditary (germline) and non-hereditary (somatic) genetic components. Understanding the genotype-phenotype correlation of variants in the context of clinical, therapeutic, pharmacokinetic, reproductive, developmental, behavioral, functional, nutritional, athletic, morphological, and aesthetic phenotypes is a major component of applied genetics and genetic testing. For example, in monogenic diseases, genetic variants can be considered to be "pathogenic" or "benign." However, many genetic variants are of "unknown" or "uncertain" clinical significance because they have not been or cannot be clearly associated with a clinical phenotype. With an abundance of variants of unknown or uncertain clinical significance (VUS) and changing interpretations of variants, the ability to predict the functionality (phenotypic impact) of genetic variants represents a significant hurdle to accurate interpretation of variants in genetic tests. Accordingly, FIG. 12 depicts a process in which machine learning models that leverage nested coevolution improves the ability to predict functionality of residue variants of a particular biomolecule. Process 1200 can begin with identification of labeled variants, where the labels represent known categorical or numerical values associated with specific variants. In the case of categorical labels, labeled variants are assigned to a category from a set of categories. Two common categories for variants are true positive and true negative, where true positive variants are known to be associated with a particular phenotype and that true negative variants are known to lack that particular phenotype (1201). However, the number of categories need not be limited to two. In the case of numerical labels, labeled variants are assigned a known quantitative trait, such as the quantitative clinical phenotype caused by specific variants. For example, the conductivity of sweat in cystic fibrosis patients is a specific phenotype modulated by variants in the CFTR gene. The sets of labeled variants can be derived from any dataset having this information, such as publicly or privately available database. Examples of available databases are described above. Residue variants without labels are termed unlabeled variants.

Process 1200 can continue by assigning categorical or numerical features to each labeled and unlabeled variant, such as the residue-specific nested coevolution sector scores. Residue-specific conservation scores, residue-specific structural characteristics, physicochemical features of the variant and residues. (1203). The features may include any appropriate description for the variant or the affected residue, and thus may describe characteristics that are, for example, biochemical, biophysical, functional, evolutionary, populational (demographic), or structural in nature. These features may be proprietary, or publically available, such as population frequency in the Exome Aggregation Consortium or published amino acid substitution matrices).

Process 1200 can continue by training a machine-learning model on the set of labeled variants and their features (1205). Examples of common machine learning models include Random Forests (RFs), Gradient Boosted Trees (GBMs), Support Vector Machines (SVMs), and Ensemble Voting Classifiers (EVCs), as well as models based on neural network architectures such as Artificial Neural Networks (ANNs), Dynamic Neural Networks (DNNs), Feedforward Neural Networks (FNNs), Recurrent Neural Networks (RNNs), Probabilistic Neural Networks (PNNs), Convolutional Neural Networks (CNNs or Perceptrons), Instantaneously-Trained Neural Networks (ITNNs), and others (S. B. Kotsiantis, *Informatica*, 31, 249-268 (2007), the disclosure of which is incorporated herein by reference).

Process 1200 can continue by using the trained model to predict the categorical or numerical label of variants, such as variants not included in the training of the machine-learning model. Features of the unlabeled variant are assigned to the unlabeled variant, and inputted into the trained machine learning model. The model then makes a prediction as to the label of the unlabeled variant.

Process 1200 can continue by consolidating predictions of labels into a datasets and/or databases (1213). Reports of these data can be produced (1209) and displayed (1211). Additionally, these data can be used to diagnose samples from genetic tests by assessing the variants in the sample (1215). The sample may be derived from any appropriate biological source, including, cell lines, patient biopsies, bacteria, viruses, or any other biological tissue.

Exemplary Embodiments

Biological data supports the methods and systems of building biomolecule coevolution data structures, matrices, sector scores, and applications thereof. It is noted that embodiments of the invention identify coevolution of residue positions on multiple evolutionary distances. The resulting coevolution matrices can identify biomolecule sectors that can further be exploited to predict functions or structures of unlabeled residue variants.

Biomolecular Coevolution Analysis and Robustness: β-Actin

Figure 13:
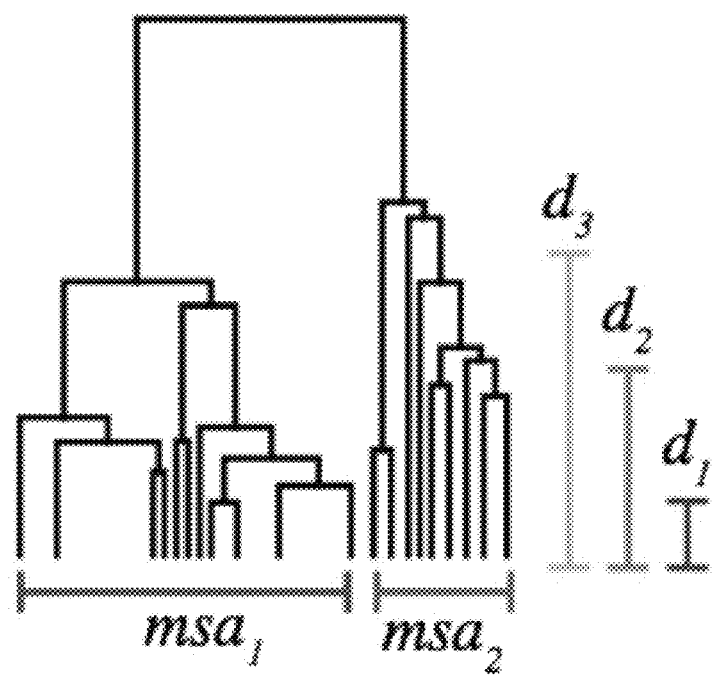
FIG. 13 illustrates an example of a phylogenetic tree generated in accordance with various embodiments of the invention.
Figure 14:
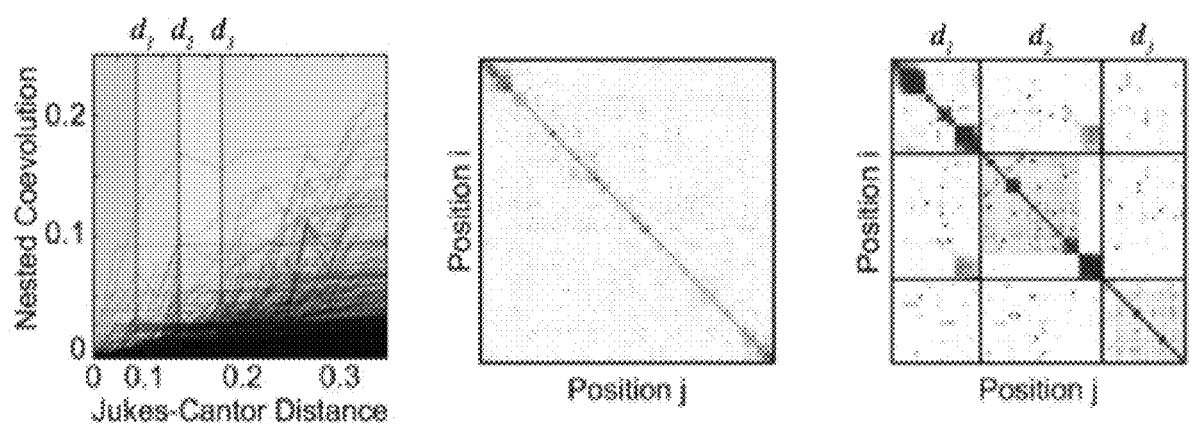
FIG. 14 illustrates examples of β-actin intra-clade covariation on various timescales generated in accordance with various embodiments of the invention.
Figure 15:
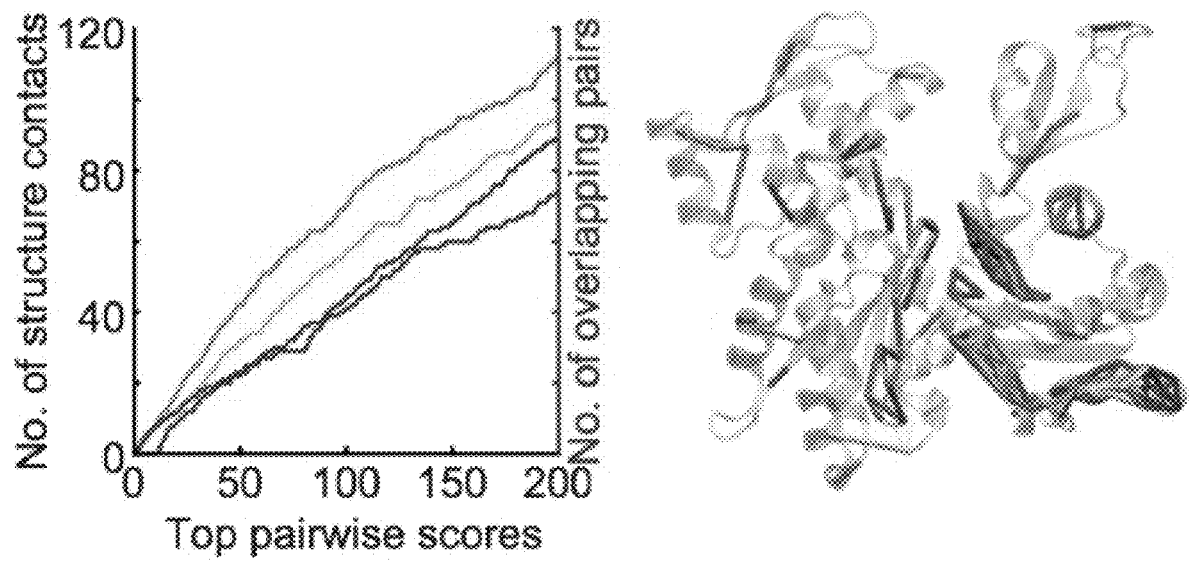
FIG. 15 illustrates structure contacts and overlapping pairs of β-actin residues predicted by nested coevolution generated in accordance with various embodiments of the invention.

To determine the nature and functional significance of the information encoded in the phylogenetic dimension of nested coevolution, β-actin (Seq. ID No. 15) was analyzed as a representative example. β-actin is a dynamic cytoskeletal protein with many physiological roles for which a number of pathogenic missense mutations have been identified. Specifically, the contribution of covariation signal as a function of the phylogenetic cutoff was considered (FIG. 13). As in previous studies, positions with high conservation (Shannon entropy <0.1) or composed of more than 25% gaps in the MSA were excluded. As the phylogenetic cutoff was varied, there were increases in covariation signal between each set of adjacent cutoffs for particular pairs of residues, with some pairs experiencing a high degree of covariation with small phylogenetic cutoffs (FIG. 14, left panel). These distinct groups of residue pairs that cluster based on their coevolution evolutionary distance also tended to coevolve collectively (FIG. 14, middle and right panels). As with other highly conserved proteins, the pairs of residues with the largest signals within each phylogenetic window exhibited enrichment of known structural interactions (FIG. 15), and these pairs formed groups of residues that were spatially compact on the protein's structure (FIG. 15). Taken together, these observations suggest that the phylogenetic dimension of coevolution represents novel signal that can be leveraged to gain information pertinent to protein structure.

To assess the robustness of nested coevolution predictions to the sampling of sequences in a MSA, as a representative example, measurements were repeated for β-actin on two disjoint subsets of sequences from the original MSA that were maximally separated (FIG. 13). The sequences of the MSA of β-actin was sorted by Jukes-Cantor distance to the reference sequence, and subsequently split into two groups of equal sequence number. The full and nested coevolution was measured at a single phylogenetic cutoff for each MSA. The rank sum was measured for the calculated metric for every pair of corresponding calculations between the two MSAs.

Figure 16:
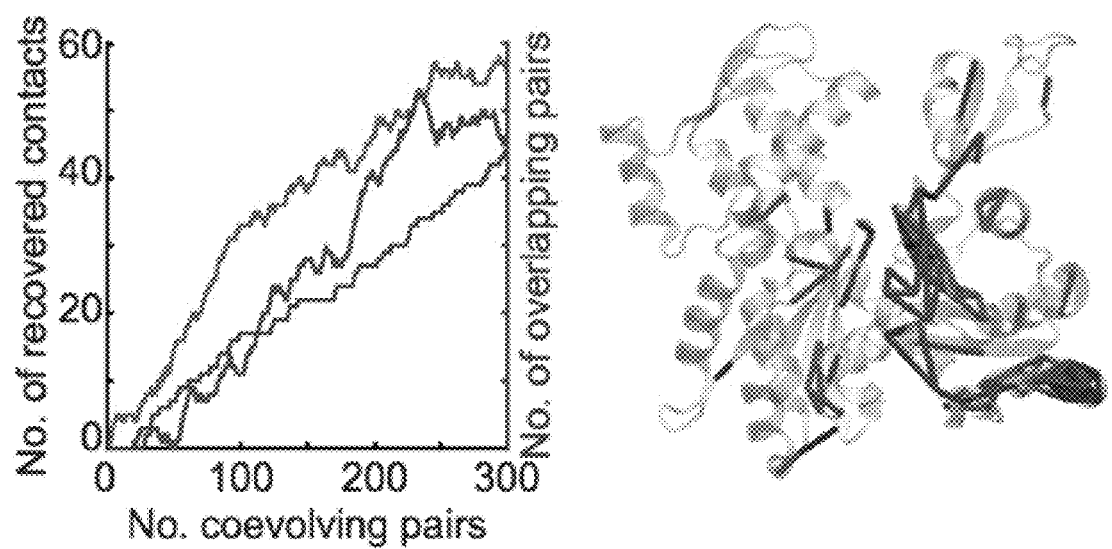
FIG. 16 illustrates recovered contacts and overlapping pairs of β-actin positions predicted by nested coevolution generated in accordance with various embodiments of the invention.

For both MSAs, the intra-clade covariation measured with small phylogenetic cutoffs recovered nested coevolution signal more enriched in structural contacts than the full covariation (FIG. 16). Interestingly, the groups of residue pairs with the highest nested coevolution signal calculated from either MSA were only partially overlapping, suggesting subtle functional differences between sequences within each MSA. Nonetheless, the groups spanned similar compact regions when mapped onto the protein structure (FIG. 16; UniProt Protein Data Bank ID (PDBID): 1YAG).

The spatial contiguity of coevolving residue groups is consistent with the notion that the nested coevolution among these residues results from structural or functional interactions. To test whether residues signifying strong nested coevolution are functionally important, the nested coevolution matrix of human actin (ACTB) was computed, and coevolving residues were compared with known pathogenic missense mutations (excluding those at highly conserved positions). To identify groups of coevolving residues, principal component analysis (PCA) of the nested coevolution signal across multiple phylogenetic windows was conducted. Confirmed and likely pathogenic mutations in ACTB gene (coding for cytoplasmic actin 1, refseq transcript NM_001101, were downloaded from the ClinVar website in May 2016). Positions of high conservation (entropy <0.1) were excluded from the analysis. The p-value of the left- and right-tailed rank-sum between known pathogenic and all other low-conservation (entropy >0.1) positions was calculated for the first 5 eigenvectors, and corrected using Benjamini-Hochberg multiple hypothesis correction.

The eigenvector ranksum analysis results revealed that pathogenic mutations were highly enriched in the top 10 eigenvectors of nested coevolution (FIG. 14, $p<0.005$, false discovery rate-adjusted q-value $<0.05$ by Wilcoxon rank-sum test). Thus, nested coevolution sector reveals functionally relevant residues in actin in a manner that complements the importance of conservation.

Coevolution and Mutational Burden in an Oncogene: PIK3CA

As explained in the previous section, coevolution can detect signatures of functionality on the relatively short evolutionary timescales of adaptation within human tumors. As an additional case study, this analysis focused on PIK3CA (Seq. ID No. 16), a gene encoding the catalytic subunit of PI3K alpha polypeptide, p110-α, that has been found to be mutated in a range of human cancers. Using The Cancer Genome Atlas (TOGA) database, nested coevolution predictions of functional residues in p110-α was evaluated by measuring the Wilcoxon rank-sum test between the residues associated with the nested coevolution eigenvectors with the highest eigenvalues, and the positions of observed somatic missense mutations across 16 tumor types and pan-cancer (three cancers were excluded due to low frequency of missense mutations in PIK3CA). The unique positions of missense somatic mutations in PI3K were aggregated for each cancer type. Highly-conserved positions (Shannon entropy <0.1) were excluded from this analysis. Nested coevolution was measured on non-human sequences. The Wilcoxon rank sum test between mutations position and non-mutated positions was calculated for the top eigenvector of nested coevolution for each cancer type, and for the pan-cancer set of mutations. The analysis was repeated using Shannon entropy in place of the top eigenvector.

Figure 17:
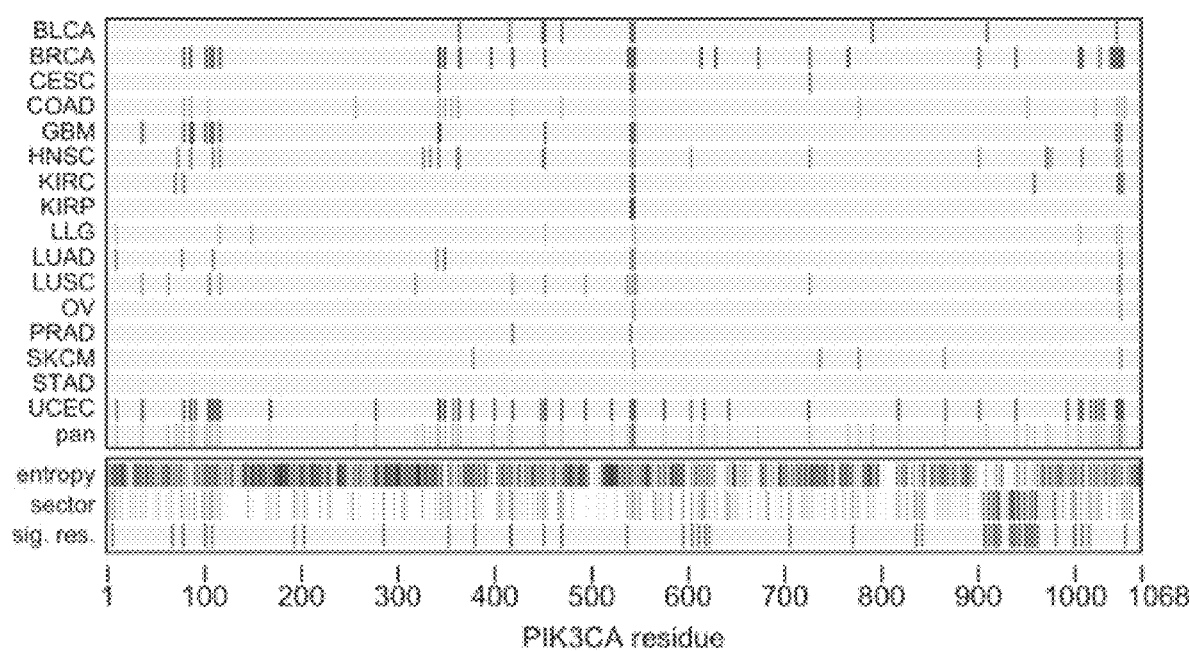
FIG. 17 illustrates the position of the catalytic subunit alpha of PIK3CA, p110-α, with observed mutations of multiple cancers generated in accordance with various embodiments of the invention.
Figure 18:
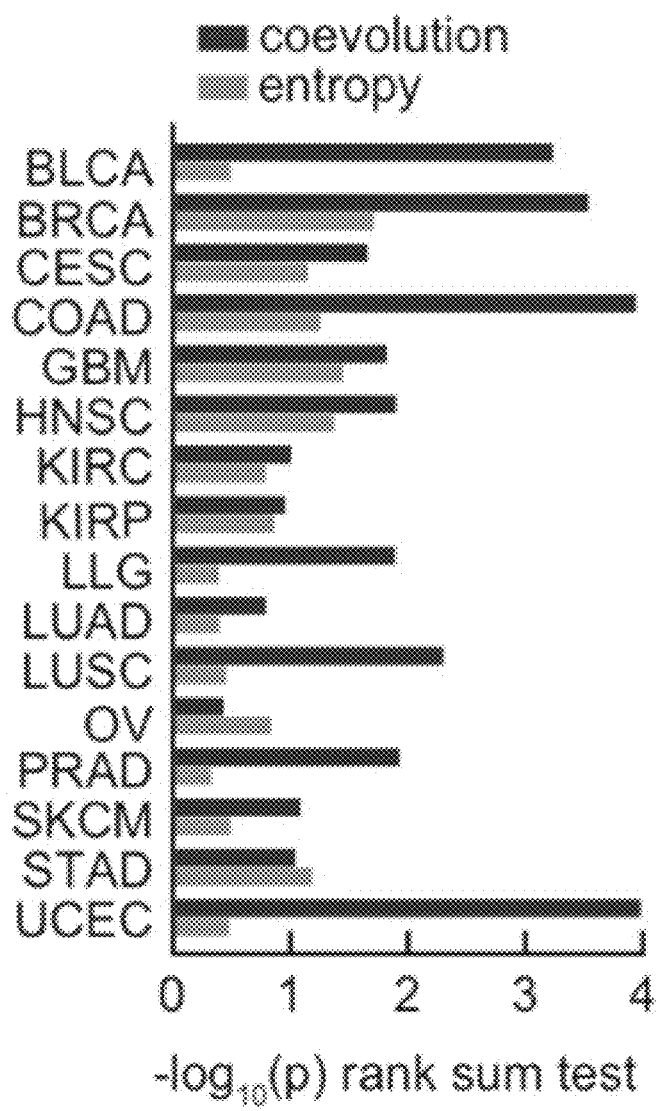
FIG. 18 illustrates rank correlations of mutations with nested coevolution vectors generated in accordance with various embodiments of the invention.
Figure 19:
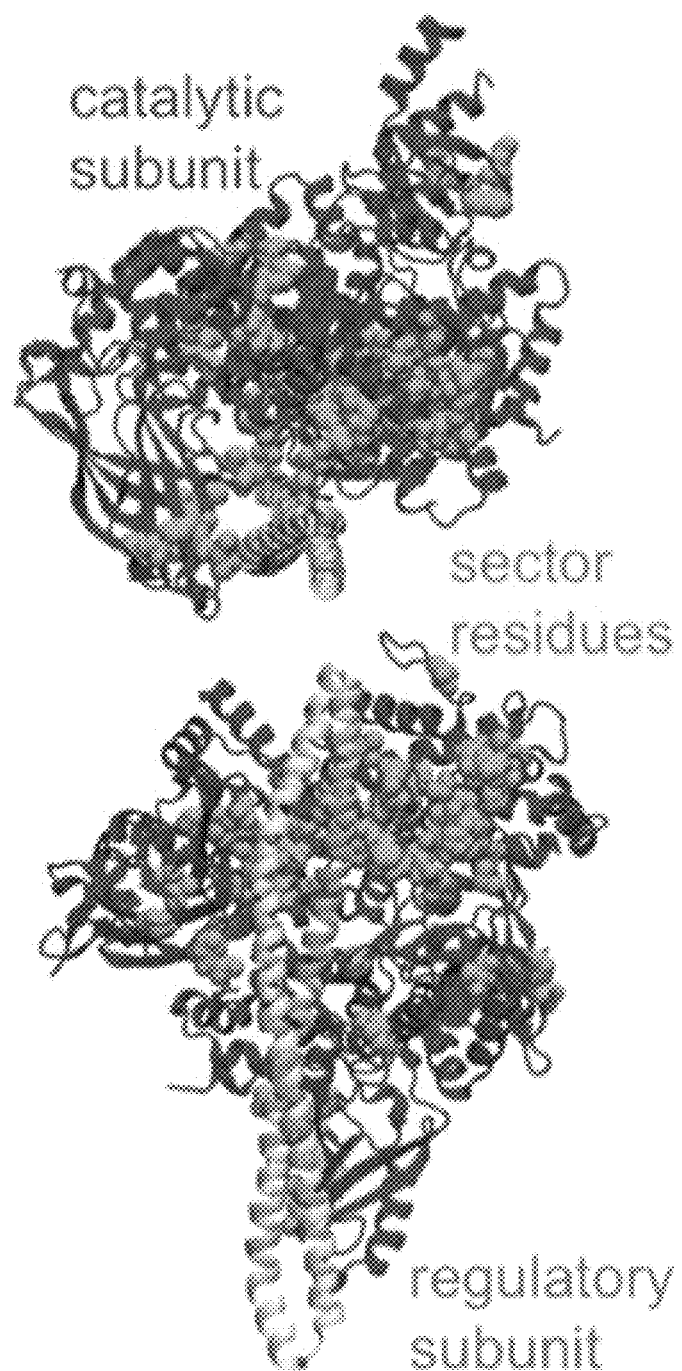
FIG. 19 illustrates the positions of p110-α that most strongly associated with the most significant biomolecule sector derived from a nested coevolution matrix generated in accordance with various embodiments of the invention.

Although the background distribution of missense mutations was highly variable across different cancer types (FIG. 17), missense mutations in p110-α exhibited significant enrichment for positions associated with the nested coevolution eigenvector with the highest eigenvalue across multiple cancers (FIG. 18), suggesting that somatic point mutants in p110-α leading to cancer occur preferentially in a network of highly coevolving residues. Importantly, there was no significant correspondence between positions of high conservation (entropy) and missense mutations in p110-α (FIG. 18), demonstrating that coevolution signal is distinct from conservation. Moreover, the positions associated with the first nested coevolution eigenvector (FIG. 17) mapped onto a nearly contiguous sector on the protein structure (FIG. 19, PDB ID: 5FI4) known to interact with the PI3K regulatory subunit p85-α.

Figure 20:
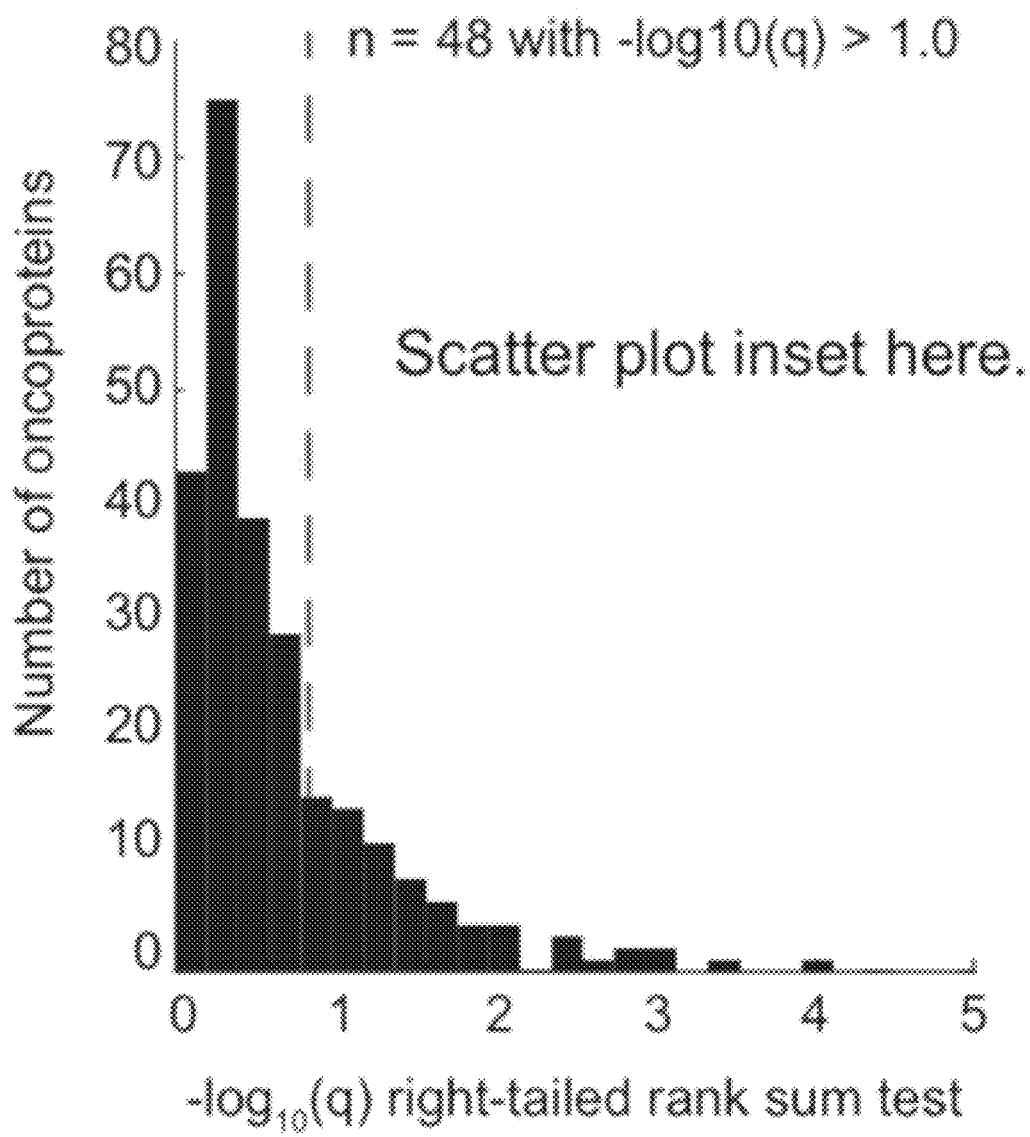
FIG. 20 illustrates pan cancer analysis of oncoproteins with missense mutations that significantly overlap with coevolving positions generated in accordance with various embodiments of the invention.

The PI3K analysis was extended to pan-cancer missense mutations across 258 oncoproteins from TCGA database, except that the rank sum was calculated for all nested coevolution eigenvectors corresponding to the top 80% of variance, as determined by the corresponding eigenvalues, with a Benjamini-Hochberg multiple hypothesis correction for the p-values from each protein's set of eigenvectors and the minimum q-value was aggregated for each protein. After correcting for multiple-hypothesis testing, 48 oncoproteins with statistically significant correspondence between the positions of missense mutations in tumors and residue clusters predicted by nested coevolution were identified (Wilcoxon rank-sum test, FDR-adjusted q-value <0.1, FIG. 20). Taken together, these measurements demonstrate a close relationship between evolutionarily determined protein clusters and sites of recurrent mutation in tumors. The statistically significant enrichment of less common somatic mutations with sectors suggests that nested coevolution can be used to assess whether such variants are pathogenic or simply result from the high mutations rates in tumors, potentially providing a new window into the interpretation of disease-causing missense mutations.

Nested Coevolution and Predictive Diagnostics: BRCA1

As described in the previous two sections, nested coevolution can detect signatures of functionality on the relatively short timescales of adaptation within human tumors. By further applying this knowledge, coevolution can be used to predict pathogenicity of mutations in genes related to oncogenesis. Traditional methods relied on a post hoc "wait and see" approach to determine the pathogenicity of mutation in an oncogene. This approach yields pathogenicity about particular mutations only after the onset of oncogenesis. Thus, it is desirable to be able to acquire a protein sequence of interest and be able to predict the pathogenicity of the mutations acquired in order to begin an appropriate therapeutic regimen to prevent the onset or further development of neoplastic activity.

Figure 21:
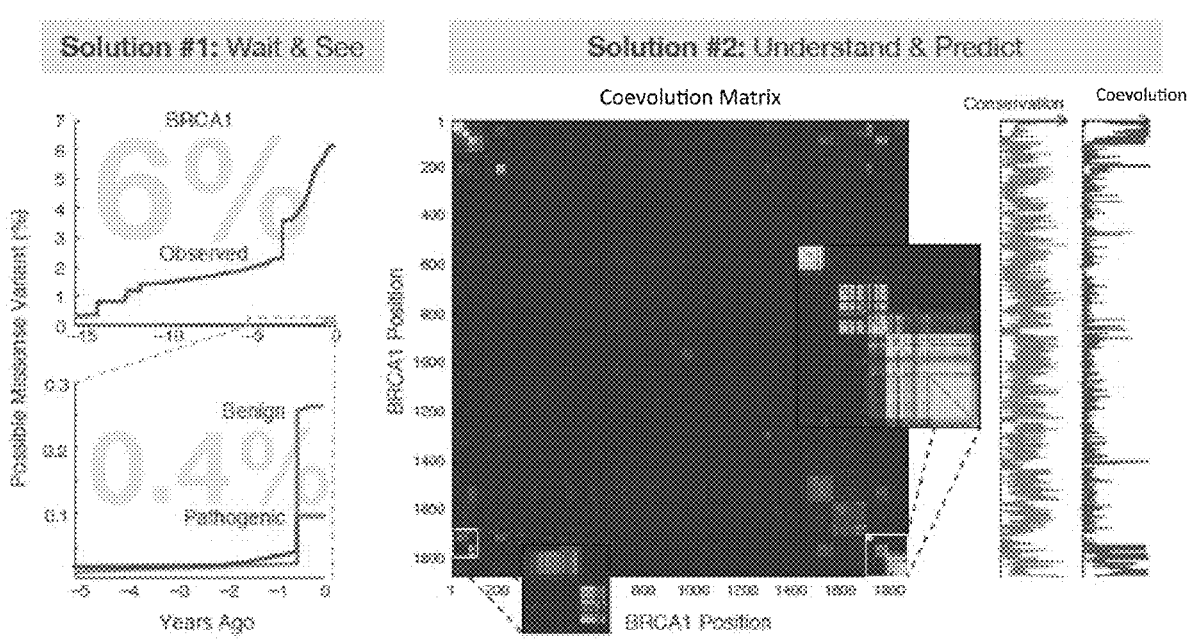
FIGS. 21-22 illustrate missense variant pathogenicity classification using a either a "wait and see" approach and or a nested coevolution-powered machine learning-based prediction method generated in accordance with various embodiments of the invention.

FIG. 21 depicts an example of oncogenesis; comparing the "wait and see" approach with predictions based on coevolution. On the left panel, a time-series of the variant coverage of the post-hoc method was determined by plotting the number of unique BRCA1 (Seq. ID No. 17) variants observed (purple line), and the number of unique BRCA1 variants with benign and pathogenic interpretations (blue and red respectively); as determined by data extracted from the publically available ClinVar database. In the right panel, a nested coevolution matrix at a particular phylogenetic distance was generated for a multiple sequence alignment of BRCA1. The value of conservation and maximum nested coevolution is calculated separately for each position, as the green and blue lines respectively.

In the "wait and see" approach, missense variants in the breast cancer oncogene BRCA1 were added to the ClinVar database approximately 15 years ago (FIG. 21, left side). Currently, 6% of possible missense variants are observed. In contrast, only 0.4% of variants are assigned (FIG. 21, left side, zoomed in graph). Of these assigned variants, 0.1% are pathogenic and 0.3% are benign. The vast majority of the observed variants (5.6% of the 6%), however, remained undiagnosed, and 95% of unobserved variants that could be observed in the future also remain unlabeled.

Nested Coevolution analysis can provide a predictive diagnostic to better understand the missense variants that develop over various evolutionary distances. As shown in the Nested Coevolution Matrix in FIG. 21, several residue positions are coevolving together. In particular, the zoomed in insets of the matrix show that various residue positions of BRCA1 are coevolving together. The inset on the left shows that various residues around 1700-1800 are significantly coevolving with residues 1-100. The inset on the right shows very strong coevolution of the C-terminal residues with other C-terminal residues. These coevolution signals are distinct and robust when compared to basic entropy conservation signals (FIG. 21, right pictographs).

Figure 22:
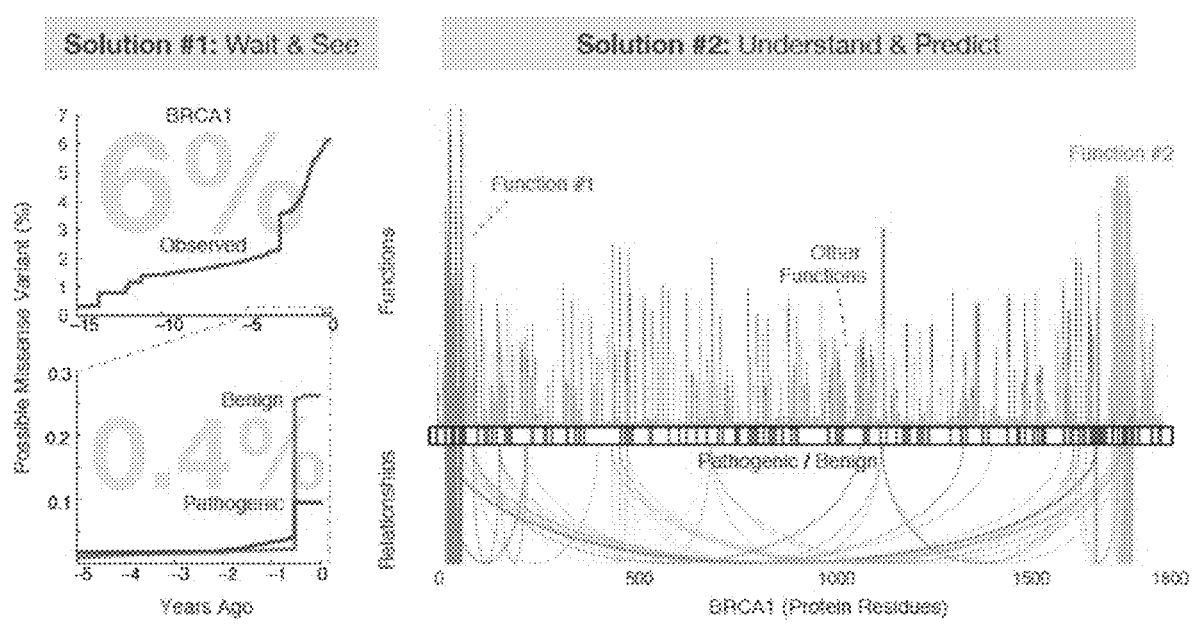

Eigenvectors decomposed from the BRCA1 coevolution matrix yields sectors of highly coevolving positions (FIG. 22, right panel). Two sectors, labeled Function #1 and Function #2, are more prominent than the rest of the sectors (shown in gray as other functions). Function #1 was found to signal strong coevolution relationships among several N-terminal residues, and some relationships between N- and C-terminal residues (FIG. 22). Function #2 primarily signaled strong relationships between C-terminal residues.

When sector scores are calculated (eigenvectors are decomposed) and biomolecule sectors are computed, the biomolecule sectors are initially unlabeled to any structure or function. The biomolecule sectors simply signify cohorts of residue positions that are coevolving together. Biomolecule sectors can be assigned a structure or function, however, when they significantly align with known structure or function as defined by a database. Accordingly, pathogenic and benign variants and indels from the ClinVar database were plotted along the BRCA1 peptide chain and overlayed with the sector signals (FIG. 22, right panel). This overlay demonstrates that Function #1 and Function #2 have strong coevolution signals at residue positions that known to be pathogenic. Thus, Function #1 and Function #2 can be assigned a pathogenic function and can predict that variants that fall within that sector are also likely to be pathogenic. The Other Functions, represented by other eigenvectors, did not significantly overlay with pathogenic positions and therefore cannot be leveraged to predict pathogenic variants.

Figure 23:
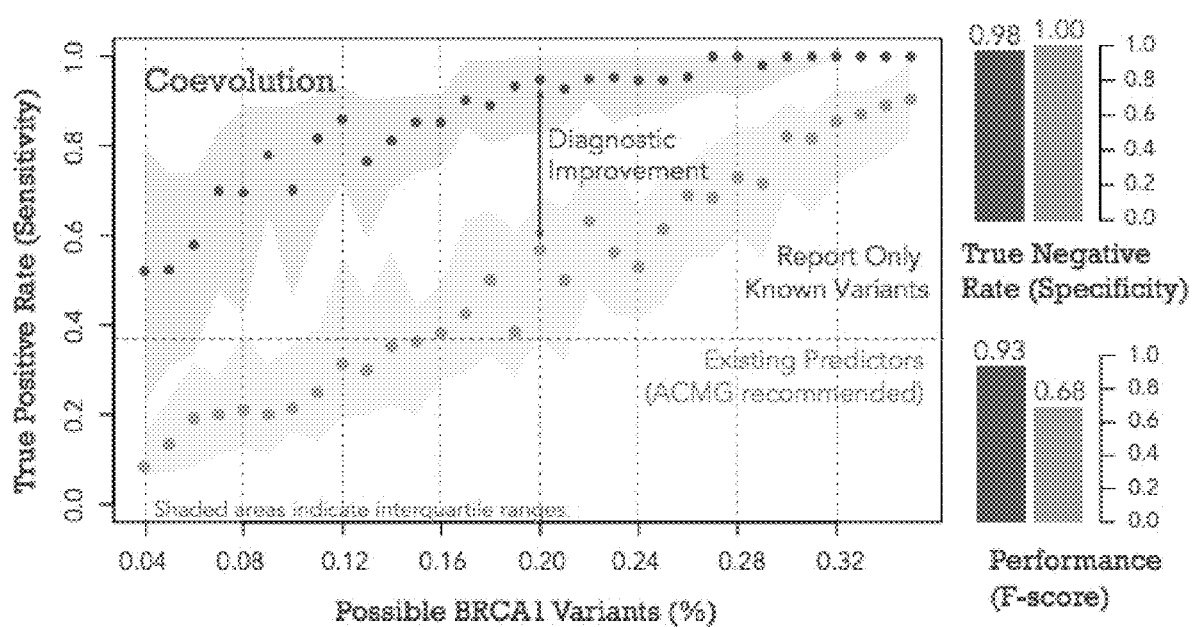
FIG. 23 illustrates the diagnostic gains of using machine learning models trained with nested coevolution generated in accordance with various embodiments of the invention.
Figure 24:
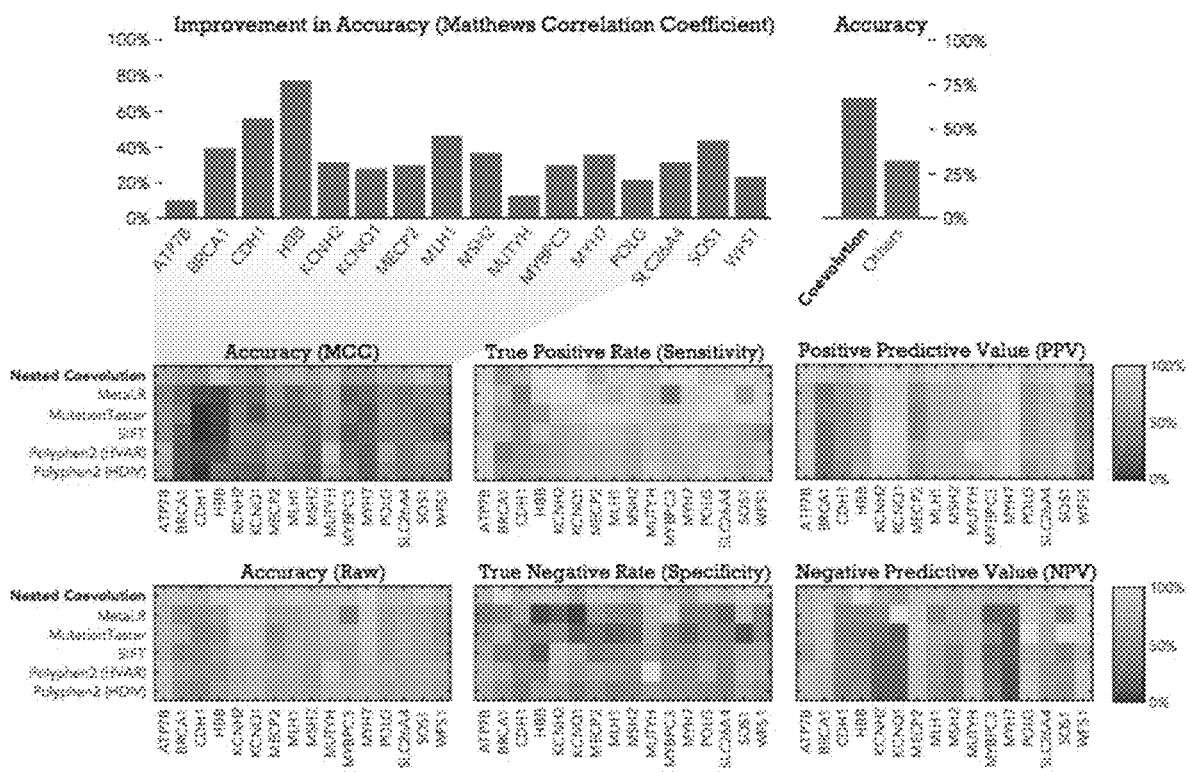
FIG. 24 illustrates the diagnostic gains of using machine learning models trained with nested coevolution across 16 disease-associated genes, compared to 5 common variant effect predictors, generated in accordance with various embodiments of the invention.

Coevolution prognostication can be significantly improved by machine learning. As more variants with known function are assigned to a biomolecule sector, the ability to predict unlabeled variants significantly improves. FIG. 32 demonstrates that as more BRCA1 variants are assigned, the ability to predict the pathogenicity of unlabeled variants increases. Standard practice of reporting only known variant pathogenicity is shown in light gray. Standard practice reveals a linear line that as the percentage of variants with known pathogenicity increases, the ability to predict pathogenicity increases at a 1:1 ratio. Thus, if 50% of variant pathogenicity is known, standard practice can predict 50% of pathogenic variants based on this knowledge. Existing predictors of pathogenicity have an accuracy of less than 40%, as shown by the horizontal dashed line. Coevolution, on the other hand, can improve the sensitivity of diagnostics by approximately 36% (FIG. 23, dark line). Knowing just 10% of the pathogenicity of the variants, ~50% of the variants can be predicted. Likewise, knowing 50% of the variants can predict ~86%. The increased sensitivity of coevolution did not reduce the specificity, as the True Negative rate was very near perfect (0.98). Coevolution's accuracy was also very good, with an F-score of 0.93. FIG. 24 shows similar results for 16 disease-associated genes. In all 16 cases, the nested-coevolution based machine learning model improves the diagnostic performance of classification performance for unlabeled variants, as measured by multiple common of diagnostic metrics of performance, compared to several existing variant prediction software, showing on average. In sum, coevolution offers significantly improved diagnostic performance of variant effect predictions.

Doctrine of Equivalents

While the above description contains many specific embodiments of the invention, these should not be construed as limitations on the scope of the invention, but rather as an example of one embodiment thereof. Accordingly, the scope of the invention should be determined not by the embodiments illustrated, but by the appended claims and their equivalents.

Sequence Listing

The current disclosure incorporates sequence listing in accordance with the WIPO Standard ST.25, The Sequence listing embodies 17 protein sequences (Seq ID Nos. 1-17), which are referenced throughout the specification,

What is claimed is:

1. A method for performing a genetic test that predicts phenotype of unlabeled residue positions with machine learning on a patient's biological sample, the method comprising:
  receiving nested coevolution sector scores of a biological sample using a computing system, wherein the biological sample is derived from a patient, and wherein the nested coevolution sector scores are generated by:
    receiving multiple sequence alignment data for a particular biomolecule using the computing system, wherein the multiple sequence alignment data comprises homologous sequences of the particular biomolecule, and wherein the multiple sequence alignment data comprises sequence data of the biological sample;
    computing a plurality of total covariation values of each pair of residue positions within the multiple sequence alignment data using the computing system;
    defining at least two clades within the multiple sequence alignment data using the computing system based upon at least one phylogenetic cutoff,
      wherein each phylogenetic cutoff is defined by an phylogenetic distance, and
      wherein each clade is a group of sequences within the multiple sequence alignment data that have an phylogenetic distance equal to or below a particular phylogenetic cutoff;
    computing inter-clade covariation values of each pair of residue positions within the multiple sequence alignment data for each particular phylogenetic cutoff using the computing system, wherein the computed inter-clade covariation values are covariation signals attributed to phylogenetic drift;
    computing intra-clade covariation values of each pair of residue positions for each particular phylogenetic cutoff using the computing system, wherein the computation of intra-clade covariation values removes covariation signals attributed to phylogenetic drift;
    building an intra-clade covariation matrix describing the intra-clade covariation values of each pair of residue positions for each particular phylogenetic cutoff using the computing system, wherein the intra-clade covariation matrix comprises a matrix of intra-clade covariation values between residue positions for each particular phylogenetic cutoff;
    building a nested coevolution matrix that integrates signal from at least one intra-clade covariation matrix;
    generating coevolution sectors scores for each residue of the biomolecule sequence by applying a dimensionality reduction technique using the computing system;
  receiving sets of data describing residue variants labeled with a numerical or categorical label using the computing system, wherein the data describing the labeled residue variants comprises residue variants labeled as true positive for a phenotype and residue variants labeled as true negative for the phenotype;
  assigning at least one feature to the labeled residue variants using the computing system, wherein the at least one feature comprises the nested coevolution sector scores;
  training a machine learning model on the set of labeled residue variants with at least one assigned feature using the computing system;
  utilizing the machine learning model to predict the phenotype of at least one unlabeled variant within the particular biomolecule sequence using the computing system, wherein the unlabeled variant exists within the sequence data of the biological sample, and wherein the phenotype is equated with the labeled phenotype of the true positive variants or the false positive variants; and
  diagnosing the biological sample based on the predicted phenotype of the at least one unlabeled variant.

2. The method of claim 1, wherein multiple phylogenetic cutoffs are used to build multiple matrices of intra-clade covariation values.

3. The method of claim 1, wherein the inter-clade covariation values are computed analytically or by bootstrapping.

4. The method of claim 1, wherein the phylogenetic distance is determined by the an evolutionary rate model, wherein the evolutionary rate model is as the Jukes-Cantor model, the Kimura model, the Felsenstein model, the Tamura model, the Dayhoff model, or the Goldman and Yang model.

5. The method of claim 1, wherein the biomolecule is a protein related to disease.

6. The method of claim 1, wherein the dimensionality reduction technique generates eigenvectors based on an eigendecomposition of the nested coevolution values within the nested coevolution matrix using the computing system, wherein sector scores correspond to the eigenvectors and have associated eigenvalues determined by the eigendecomposition.

7. The method of claim 1, wherein the total covariation is calculated by the equation:

$$C_T^{ij}=(H_i+H_j-H_{i,j})/H_{i,j}.$$

8. The method of claim 1, wherein the dataset is a publicly or privately available database.

9. The method of claim 1, wherein the dataset is a database of relationships between human genetic variants and clinical phenotypes.

10. The method of claim 1, wherein the phenotype is clinical phenotype.

11. The method of claim 1, wherein the machine learning model is Random Forests or Gradient Boosted Trees.

12. The method of claim 1, wherein the intra-clade covariation values are computed by subtracting the inter-clade covariation value of each pair of residue positions from the total covariation value of each pair of residue positions using the computing system.

\* \* \* \* \*